United States Patent
Fang-Yen

(10) Patent No.: US 11,795,423 B2
(45) Date of Patent: Oct. 24, 2023

(54) **MICRO-FABRICATED MULTI-WELL CHIPS FOR LONG TERM AUTOMATED IMAGING OF *C. ELEGANS* GROWTH AND BEHAVIOR**

(71) Applicant: THE TRUSTEES OF THE UNIVERSITY OF PENNSYLVANIA, Philadelphia, PA (US)

(72) Inventor: Christopher Fang-Yen, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 161 days.

(21) Appl. No.: 15/318,059

(22) PCT Filed: Jun. 26, 2015

(86) PCT No.: PCT/US2015/037997
§ 371 (c)(1),
(2) Date: Dec. 12, 2016

(87) PCT Pub. No.: WO2015/200803
PCT Pub. Date: Dec. 30, 2015

(65) Prior Publication Data
US 2017/0107470 A1    Apr. 20, 2017

Related U.S. Application Data

(60) Provisional application No. 62/017,579, filed on Jun. 26, 2014.

(51) Int. Cl.
*B01L 3/00* (2006.01)
*C12M 1/32* (2006.01)
(Continued)

(52) U.S. Cl.
CPC .......... *C12M 23/12* (2013.01); *B01L 3/5085* (2013.01); *B01L 3/50857* (2013.01);
(Continued)

(58) Field of Classification Search
CPC .................. B01L 2300/0829; B01L 2200/0668
(Continued)

(56) References Cited

U.S. PATENT DOCUMENTS 4,154,795 A * 5/1979 Thorne ................. B01L 3/5085
206/460
4,599,315 A * 7/1986 Terasaki ............... B01L 3/5085
356/244
(Continued)

FOREIGN PATENT DOCUMENTS

| EP | 0 353 591 | 4/1996 |
|---|---|---|
| WO | WO 1998/046981 A1 | 10/1998 |
| WO | WO 2004/018623 A2 | 3/2004 |

OTHER PUBLICATIONS

Brenner, "The Genetics of *Caenorhabditis elegans*," Genetics 77:71-94 (1974).
(Continued)

*Primary Examiner* — Natalia Levkovich
(74) *Attorney, Agent, or Firm* — Baker Botts, LLP

(57) ABSTRACT

A composition, including a substrate having a planar array of depressions each defined by concave walls and a moat disposed around each depression of said array of depressions.

11 Claims, 24 Drawing Sheets

(51) Int. Cl.
  *C12M 1/00* (2006.01)
  *C12N 5/00* (2006.01)
(52) U.S. Cl.
  CPC ........... *C12M 23/22* (2013.01); *C12N 5/0068* (2013.01); *B01L 2300/0829* (2013.01); *B01L 2300/0858* (2013.01); *B01L 2300/10* (2013.01); *C12N 2533/00* (2013.01); *C12N 2535/10* (2013.01)
(58) Field of Classification Search
  USPC .................................................. 422/552, 553
  See application file for complete search history.

(56) References Cited

U.S. PATENT DOCUMENTS

| | | |
|---|---|---|
| 6,051,191 A | 4/2000 | Ireland |
| 6,908,594 B1 | 6/2005 | Schaevitz |
| 7,208,125 B1* | 4/2007 | Dong .................... C12M 23/12 422/42 |
| 7,998,435 B2 | 8/2011 | Reed |
| 2002/0141905 A1* | 10/2002 | Sha ....................... B01L 3/5025 422/553 |
| 2004/0228770 A1 | 11/2004 | Ghandhi et al. |
| 2007/0237683 A1 | 10/2007 | Ho et al. |
| 2007/0295741 A1* | 12/2007 | Baker .................... B65D 1/30 220/825 |
| 2011/0277425 A1* | 11/2011 | Ellson ................... C12M 23/26 53/485 |

OTHER PUBLICATIONS

Yanik et al., "Technologies for Micromanipulating, Imaging, and Phenotyping Small Invertebrates and Vertebrates," Annual Review of Biomedical Engineering, 13:185-217 (2011).

* cited by examiner

US 11,795,423 B2

MICRO-FABRICATED MULTI-WELL CHIPS FOR LONG TERM AUTOMATED IMAGING OF C. ELEGANS GROWTH AND BEHAVIOR

CROSS-REFERENCE TO RELATED APPLICATIONS

This application is a U.S. National Stage Patent Application under 35 U.S.C. § 371 of International Application No. PCT/US2015/037997, filed on Jun. 26, 2015, which claims priority to U.S. Provisional Patent Application Ser. No. 62/017,579, filed Jun. 26, 2014, the contents of each of which are incorporated by reference herein in their entirety.

FIELD OF THE INVENTION

The presently disclosed subject matter relates to scalable compositions for the cultivation and imaging of C. elegans and other organisms, as well as methods of using the same.

BACKGROUND

Aging is manifested in gradual changes in an adult organism which can cause a reduction of function and an increase in mortality rate. Certain studies of model organisms have identified highly conserved processes and pathways which influence aging, including dietary restriction, insulin/insulin-like signaling, and the cytoprotective DAF-16/FOXO pathway. The model roundworm Caenorhabditis elegans (C. elegans) has been used to study aging biology, due to its short lifespan and genetic manipulability. However, certain studies of aging in C. elegans have several limitations. First, they can focus on measurement of lifespan, an incomplete description that ignores potentially important aspects of the aging process. Second, they can rely on visual observation of worms on agar plates, a laborious and potentially-subjective process not suitable for high-throughput analysis. Third, they can be limited to studies at the population level, with individual trajectories unavailable.

To address these limitations, certain automated or semi-automated techniques for analysis of aging in C. elegans have been developed. The study of worm aging in microtiter plates under liquid culture conditions permits an increase in throughput, but also changes behavior, physiology, and lifespan. Constraining the animal to nanodroplets can result in severely compromised survival. Another method employs microfluidic chambers, which can have limited scalability and can usually be limited to specific developmental stages. One technique can employ flatbed scanners to image tens of thousands of worms on standard agar plates. However, due to a low frame rate (~1 /hr), it cannot track young adult animals or easily quantify behavior. Another study described a system for long-term multi-well imaging in glass wells, which can allow for longitudinal imaging but is not easily scalable to large numbers of worms.

In view of the foregoing, there remains a need in the art for scalable compositions for the cultivation and imaging of C. elegans, as well as other organisms, which can allow for longitudinal imaging of large numbers of organisms. In addition to applications in aging, such methods can be used for monitoring nematode development, growth, behavior, fluorescence, morphological changes, and other aspects.

SUMMARY

In certain embodiments, the present disclosure provides compositions including: a substrate having a planar array of depressions, e.g., a well, each defined by concave walls; and a moat disposed around each depression of said array of depressions. In certain embodiments, the depressions have a 3 mm diameter, a 3 mm depth, and a center-to-center spacing of 4.5 mm. In certain embodiments, the moat disposed around each depression is 0.5 mm wide and 3 mm deep. In certain embodiments, the composition is made of at least one of polyurethane, polycarbonate, polyvinyl, polystyrene, polyvinylchloride (PVC), polypropylene, cyclic olefin copolymer (COC), and polydimethylsiloxane (PDMS).

In certain embodiments, the substrate having a planar array of depressions is adapted for insertion into a tray to form a microwell assembly. In certain embodiments, the substrate is of uniform thickness. In certain embodiments, the composition is made entirely of polyurethane, polycarbonate, polyvinyl, polystyrene, polyvinylchloride (PVC), polypropylene, or cyclic olefin copolymer (COC). In certain embodiments, the composition has an overall shape and dimension generally conforming to the ANSI/SLAS microplate standard. In certain embodiments, the composition comprises at least one of a 48-well microplate having an 8×6 array of wells; a 96-well microplate having an 8×12 array of wells; a 240-well microplate having a 12×20 array of wells; and a 384-well microplate having a 16×24 array of wells.

In certain embodiments, the present disclosure relates methods of cultivating and imaging an organism, including by providing a composition that includes: (A) a substrate having a planar array of depressions each defined by concave walls; and (B) a moat disposed around each depression of said array of depressions. An organism can be introduced into a depression of said substrate, in addition to solid or liquid culture medium, any necessary food, and other reagents. The organism can be cultivated and imaged over a period of time, for example, up to several months. In certain embodiments, the organism is selected from the group consisting of C. elegans, other nematodes, zebrafish larvae, and Drosophila larvae.

BRIEF DESCRIPTION OF THE FIGURES

FIG. 1 illustrates an exemplary design, fabrication, experimental setup, and data analysis according to the disclosed subject matter.

FIG. 2 shows that an example embodiment of the disclosed subject matter generates behavioral profiles and automates lifespan analysis.

FIG. 3 illustrates lifespan prediction by behavioral profiles. FIG. 4 illustrates behavioral profiles in long-lived mutant strains.

FIG. 6 shows a comparison of image quality between standard 384-well plate and an example embodiment of the disclosed subject matter.

FIG. 7 illustrates that the well geometry of an example embodiment of the disclosed subject matter reduces burrowing and aversive moat prevents escape.

FIG. 9 illustrates automatic labeling of death time.

FIG. 11 illustrates monitoring lethargus quiescence during development.

FIG. 14 shows images of individual wells of example embodiments of the disclosed subject.

DETAILED DESCRIPTION OF EMBODIMENTS

Figure 1A:
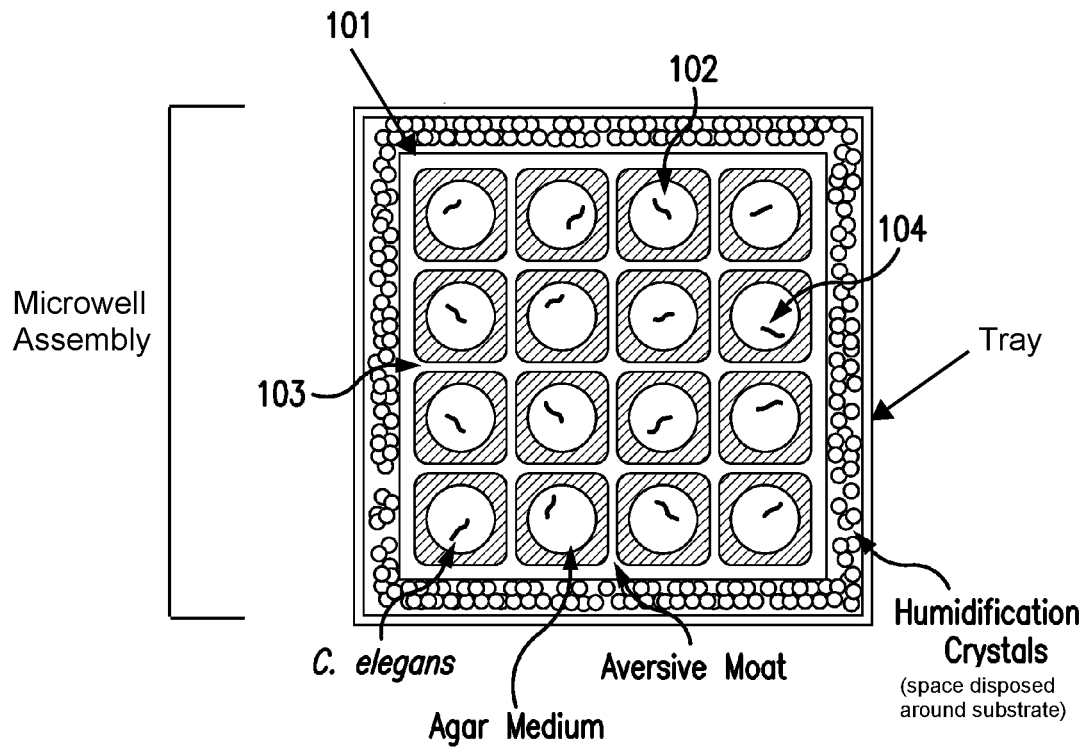
FIG. 1a shows a schematic of a 16-well example embodiment of the disclosed subject matter (top view).
Figure 1B:
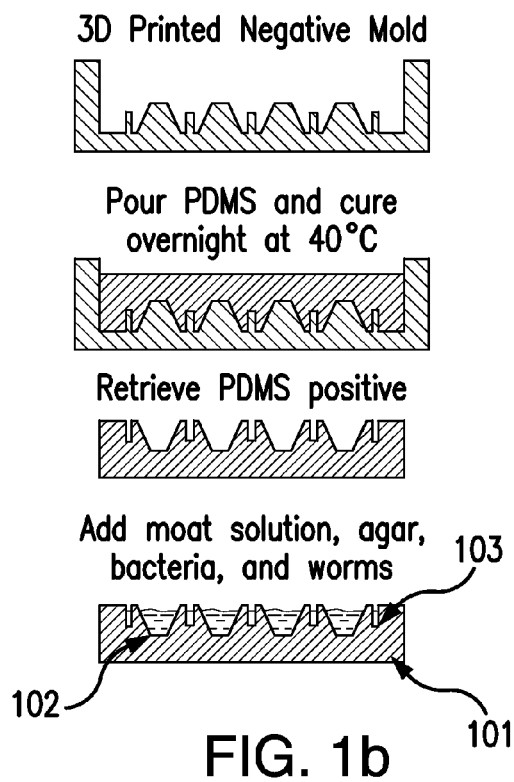
FIG. 1b shows a fabrication process (cross section).

The present disclosure provides compositions and methods for highly scalable methods of cultivating and imaging organisms, including, but not limited to *C. elegans*.

A. Construction

In certain embodiments the present disclosure provides highly scalable compositions for the cultivation and imaging of C. elegans, other nematodes, zebrafish larvae, Drosophila larvae, among other organisms. In certain embodiments, the present disclosure provides compositions including microfabricated multi-well arrays, including, but not limited to, certain embodiments identified here as the "WorMotel" ("WM").

By conforming to the ANSI standard microplate format, certain embodiments of the of the present disclosure leverage existing automation technology such as robotic plate handlers, chemical library screening, and other tools. With respect to embodiments relating to the cultivation and imaging of C. elegans, such existing automation technology also includes automated worm sorters.

In certain embodiments, the compositions, e.g., WorMotels, are constructed by manually molding polydimethylsiloxane (PDMS) from a 3D-printed master. However, mass production using injection-molded transparent polymers such as polyeurathene, polycarbonate, polyvinyl, polystyrene, polyvinylchloride (PVC), polypropylene is also possible. In certain embodiments, the compositions are fabricated from any transparent material including PDMS, polystyrene, polycarbonate, and cyclic olefin. In certain embodiments, differences in thickness throughout the composition are acceptable. In certain embodiments uniform thickness throughout the device is desirable. If uniform thickness throughout the device is desired, the composition can be produced via injection molding to achieve the desired uniform thickness.

With reference to FIG. 1, for the purpose of illustration and not limitation, in certain embodiments, the compositions of the present disclosure will include a substrate 101 including an array of wells 102. In certain embodiments, the wells are arranged in relatively close proximity in a rectangular array or matrix. Common sizes for such arrays include a 4×4 matrix (16 wells; as illustrated in FIG. 1a), an 8×6 matrix (48 wells), an 8×12 matrix (96 wells), a 12×20 matrix (240 wells), and a 16×24 (384 wells), although larger arrays can also be used that include matrices of hundreds or even thousands of wells. The size and depth of each well can be varied according to the requirements of the particular assay being developed. For example, there is a tradeoff between size of the experiments and the total number of organisms that can be simultaneously studied. In certain embodiments, the wells have a diameter of about 2 mm to about 20 mm, e.g., 3 mm diameter, and a depth of about 2 mm to about 20 mm, e.g., a 3 mm depth, and a center-to-center spacing of about 2 mm to about 20 mm, e.g., 4.5 mm.

In certain embodiments the substrate including an array of wells will be a microplate. In certain embodiments the substrate including an array of wells will take the form of an insert that can be combined with a tray to provide a microwell assembly.

Conventional 96-well or 384-well microplates are not well-suited for imaging and cultivation due to three problems. First, the vertical walls of each well make it difficult to image the organisms when they are close to the edge of the wells. Second, in instances where the wells contain agar, organisms tend to crawl between the agar and well edges, making them difficult or impossible to image clearly. Third, in certain instances, organisms can climb over the walls of the wells, mixing with other organisms in other wells.

In certain embodiments, the well geometry can improve cultivation and imaging of one organism per well. For example, but not by way of limitation, a rounded concave well geometry 105 (FIG. 1e) can reduce interference at the edge of the agar surface, and can prevent organisms from burrowing under the agar. In certain embodiments, the well array is a square array of a raised square boxes each containing a concave dimple. In certain embodiments, the space between the individual wells is a moat 103. In certain embodiments, the square box can be replaced with a cylinder containing the concave dimple. In certain of such embodiments, the moats are shaped like the space outside an array of circles.

As noted above, in certain embodiments, a moat 103 surrounds each well 102. Such moats can function to prevent organisms 104 from escaping from their individual wells. In certain embodiments, the moat disposed around each depression is between about 0.3 mm and about 1 mm wide, e.g., 0.5 mm wide, and about 2 mm to about 20 mm deep, e.g., 3 mm deep. In certain embodiments, the moat is filled with an aversive compound. In certain embodiments the aversive compound will be: copper (e.g., as $CuSO_4$) or 2% sodium dodecyl sulfate (SDS). In certain embodiments, a moat containing 100 mM copper sulfate is employed.

In certain embodiments the composition is sealed. For example, but not by way of limitation, a composition pursuant to the instant disclosure can include a microplate or microwell assembly covered by a lid. In certain embodiments, the microplate or microwell assembly is wrapped with a sealing film. In certain embodiments, the sealing film is gas permeable. In certain embodiments, Parafilm® is employed as the sealing film; however other gas permeable seals and tapes can also be used in the context of the subject matter disclosed herein.

To maintain humidity inside the microplates or microwell assemblies, water absorbing sodium polyacrylate crystals can be employed. Sterile distilled water can be added to the crystals in a ratio of 30:1 (water:crystals) by weight. Approximately 15 g of hydrated crystals can then be added around the microplates or microwell assemblies.

B. Methods of Use

In certain embodiments, the present disclosure provides methods of using the highly scalable compositions for cultivating and imaging organisms. In certain embodiments, the present disclosure provides for the use of such compositions for the long-term (>60 days) cultivation of organisms. For example, but not by way of limitation, the present disclosure provides methods of cultivating and imaging organisms, e.g., C. elegans, in studies of aging biology. The compositions of the present disclosure, e.g., the WorMotel, are well-suited for other long-term assays including the quantification of behavior during development and the monitoring of fluorescent reporters.

The methods described herein can be a powerful and scalable platform for C. elegans aging research as well as research into aging of other organisms. By tracking individually isolated organisms over their entire lifespans, the methods disclosed herein can enable longitudinal analysis of behavioral aging phenotypes. For example, as discussed herein, this analysis has uncovered previously undescribed collapse-and-revival phenotypes in C. elegans age-1 mutants. As disclosed herein, the instant methods can be used in understanding the genetic pathways and neural circuits governing aging quiescence in these and other strains.

In certain embodiments, detailed behavioral phenotypes, such as body posture, body bends, turning, and foraging can also be recorded by appropriately changing the camera's field of view and frame rate and employing existing tracking software.

Depending on the context, imaging can be carried out in a large range of spatial and temporal resolutions and over durations ranging from minutes to months.

The techniques described herein can be used for performing high-throughput screening for genetic or pharmaceutical modulators of aging in C. elegans and other organisms. For example, but not by way of limitation, the WorMotel can be designed to work with standard automation tools such as the COPAS worm sorter, liquid handlers, and robotic plate handlers. Furthermore, our approach is compatible with established RNAi protocols.

By employing near-standard culture conditions, the methods of the present disclosure can be directly compared with a large body of literature from aging studies performed on agar plates. Additionally, the organisms, e.g., worms, can remain experimentally accessible throughout their lifespans, and both the organisms and plates can be manipulated freely while maintaining the identities of the organisms under study.

In certain embodiments relating to assays of C. elegans, each well is filled with approximately 15 µL of NGM agar and seeded with bacteria. A single worm can be added to each well, either manually or using a COPAS Biosort (Union Biometrica) worm sorter. The rounded, aspheric geometry of each well can reduce interference from optical scattering at the edge of each well and to prevent worms from burrowing under the agar surface.

Figure 1C:
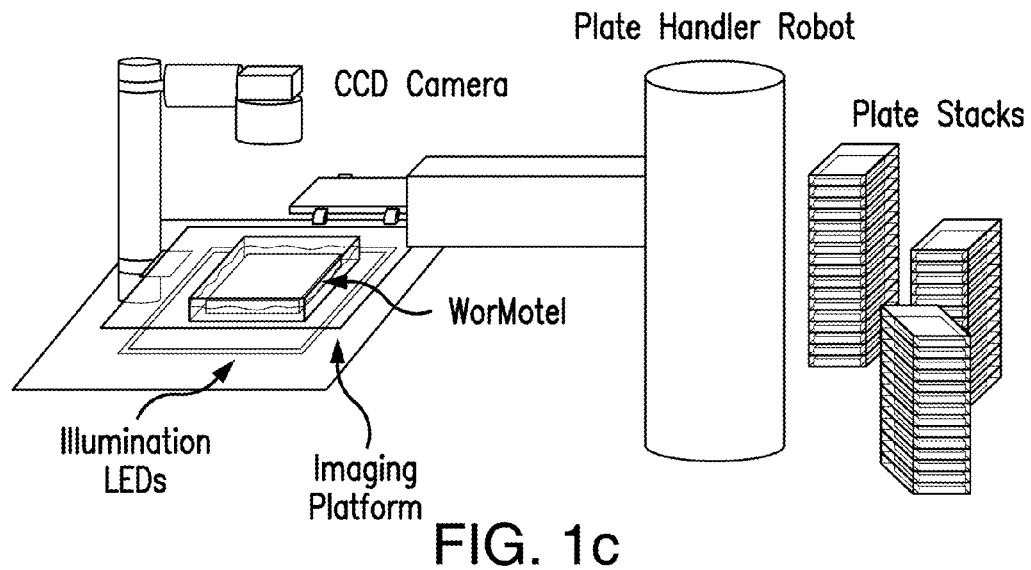
FIG. 1c shows darkfield imaging with a CCD or CMOS camera inside a light-shielded imaging rig. A robotic plate handler moves each plate from a stack to the imaging rig for 10 minute-imaging periods.
Figure 1D:
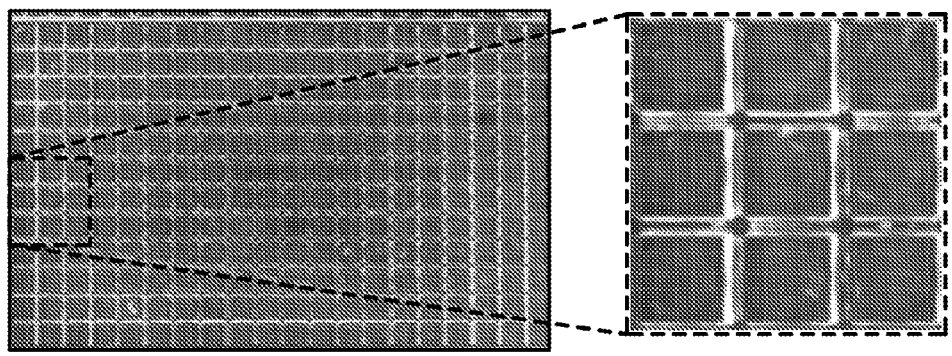
FIG. 1d shows an image of a 240-well example embodiment of the disclosed subject matter (containing L4 C. elegans). A machine vision algorithm measures activity of each worm. Distance between well centers is 4.5 mm.
Figure 1D:
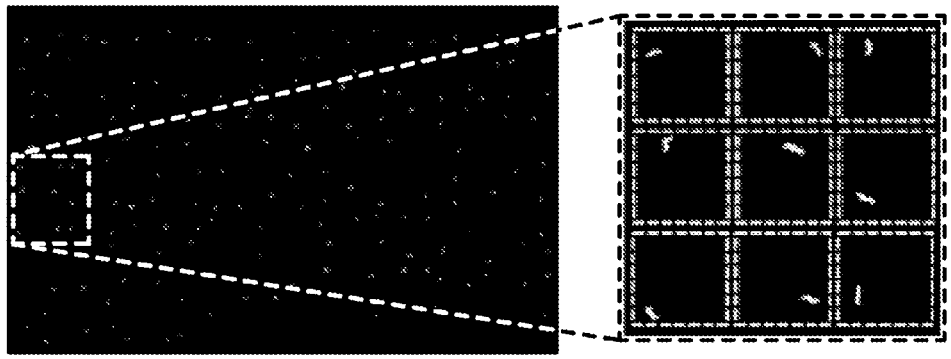
Figure 1E:
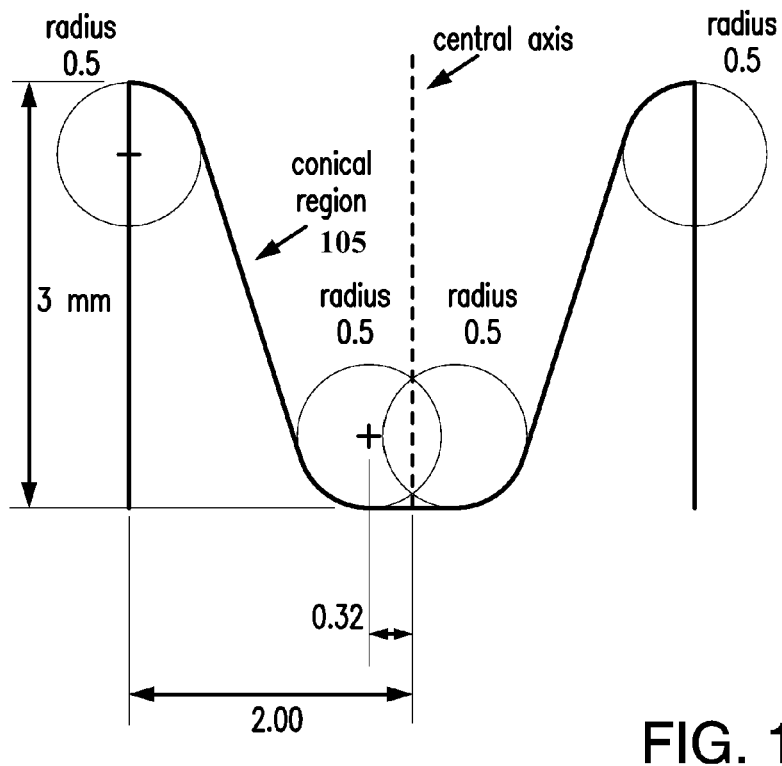
FIG. 1e shows an example of a well shape, with a cross section through center of well, where the well is symmetric around central axis.

After loading the wells, the arrays can be imaged at 0.1 frames per second or other desired temporal resolution under LED dark field illumination with an appropriate imaging system, e.g., a 5 megapixel CMOS camera (FIG. 1c). In certain embodiments there is a trade-off between number of organisms and image resolution; for example, but not by way of limitation, for a 240-well array the pixel resolution can be 36 µm when using a 5 megapixel CMOS camera. A plate handler robot with a microplate stacker can be used to serially image tens of thousands of organisms. Finally, a machine vision algorithm can quantify movement in each well between frames and records organism shape properties such as, in applications relating to C. elegans, centroid, area, and posture (FIG. 1d).

When the device is fabricated using a relatively high refractive index material, such as polystyrene (n=1.55) there can be high unwanted optical scattering from well due to a lensing effect of the rounded interface between the agar and concave well. This scattering can obscure the imaging of the organisms.

Figure 1F:
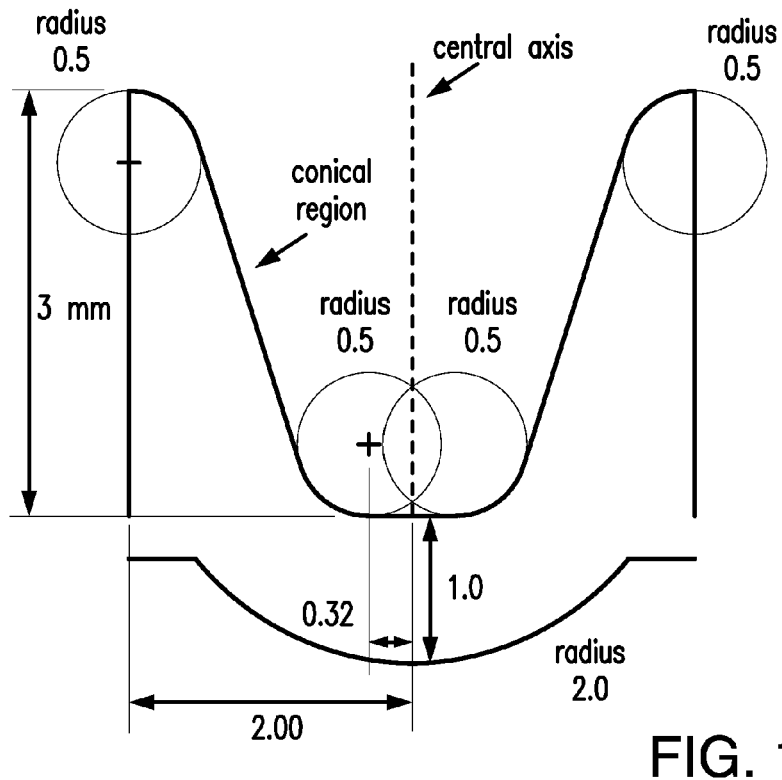
FIG. 1f shows a device having a convex rounded surface on the bottom of the device.

To address this problem, and with reference to FIG. 1f, a convex rounded surface can be provided on the bottom of the device, which is otherwise flat. The curvature of this surface can be set such that optical system consisting of the two refractive interfaces (agar-to-well-material and well-material-to-air) has a combined optical power of zero. This calculation can be performed using paraxial ray matrices or through an optical design software. For n=1.55, bottom of well radius of curvature R1=0.5 mm, and a thickness t at the optical axis (center of well) of t=1 mm, the calculation gives an optimal radius of curvature of approximately R2=2.0 mm as shown in FIG. 1f.

EXAMPLES

The following examples are put forth so as to provide those of ordinary skill in the art with a complete disclosure and description of how to make and use the presently disclosed subject matter, and are not intended to limit the scope of what the inventors regard as their presently disclosed subject matter. It is understood that various other embodiments may be practiced, given the general description provided above.

A. A Scalable Platform For Long-Term Imaging of Worm Lifespan and Behavior

Figure 5A:
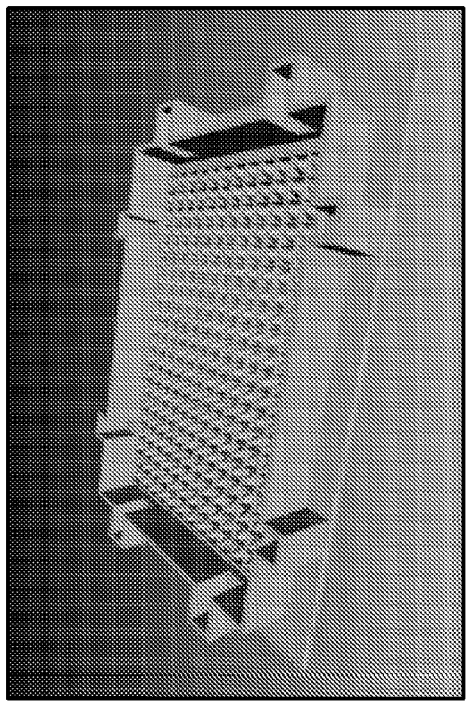
FIG. 5a illustrates a 3D rendering of well and moat geometry.
Figure 5B:
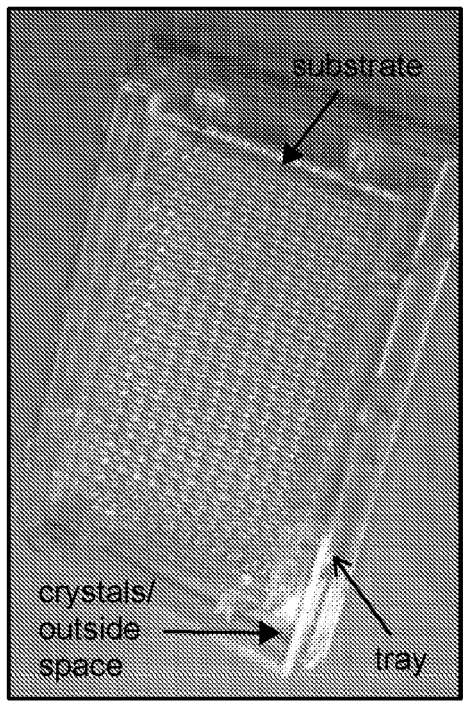
FIG. 5b illustrates a rendering of 3D printed master for a 240-well example embodiment of the disclosed subject matter including alignment tabs.
Figure 5C:
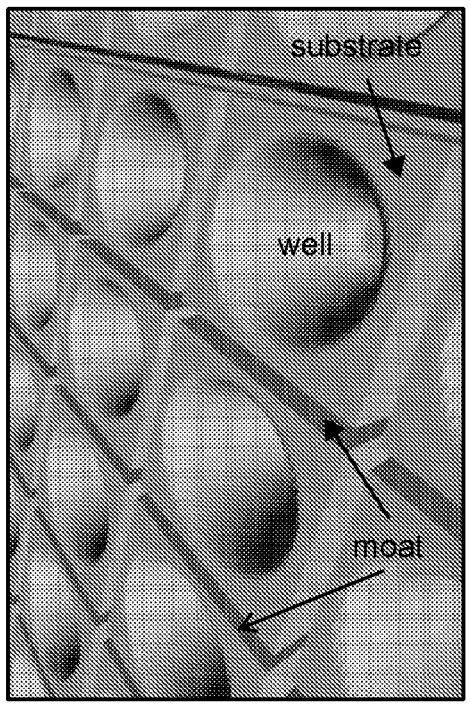
FIG. 5c illustrates a demolded PDMS device. Scale bar: 1 cm.

Each WorMotel can consist of a transparent polydimethylsiloxane (PDMS) substrate containing a rectangular array of up to 240 wells (FIG. 1a, FIG. 5), each 3-mm in diameter. To fabricate the WorMotels a novel method of molding from a 3D-printed master (FIG. 1b) was developed. Each well can be filled with approximately 15 µL of NGM agar and seeded with bacteria, which the animal feeds on. A single worm can be added to each well, either manually or using a COPAS Biosort (Union Biometrica) worm sorter. The rounded, aspheric geometry of each well can be designed to reduce interference from optical scattering at the edge of each well and to reduce worms burrowing under the agar surface (FIG. 6). A narrow liquid-filled moat surrounding each well prevents animals from escaping from their wells. After loading the devices, the arrays can be imaged at 0.1 frames per second or other desired temporal resolution under bright field or dark field illumination with a CCD or CMOS camera (FIG. 1c). There is a trade-off between number of animals and image resolution; for a 240-well array and 5 megapixel camera the pixel resolution is 36 µm. A plate handler robot with a microplate stacker can be used to serially image hundreds of plates and therefore tens of thousands of worms. Finally, a machine vision algorithm can quantify movement in each well between frames and records worm shape properties such as centroid, area, and posture (FIG. 1d).

Conventional 96-well or 384-well microplates are not well suited for worm imaging and cultivation on agar media due to three problems. First, the vertical walls of each well can make it difficult to image the worms when they are close to the edge of the wells (FIG. 6). Second, worms tend to crawl between the agar and well edges, again making them difficult to image clearly. Third, under humid conditions worms can climb over the walls of the wells, mixing with other worms in other wells.

Figure 7A:
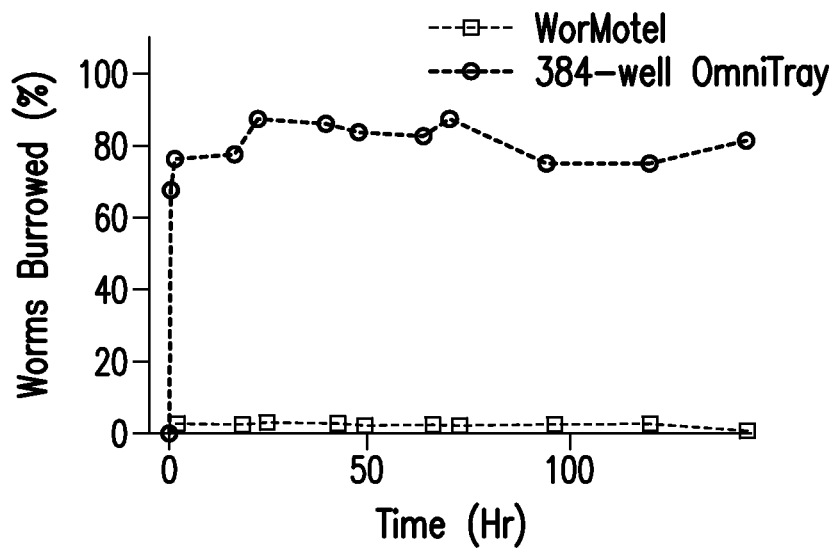
FIG. 7a shows the fraction of animals burrowing under the agar as a function of time in the example embodiment of the disclosed subject matter (red squares, n=96) and in 384-well microplate (blue circles, n=80).
Figure 7B:
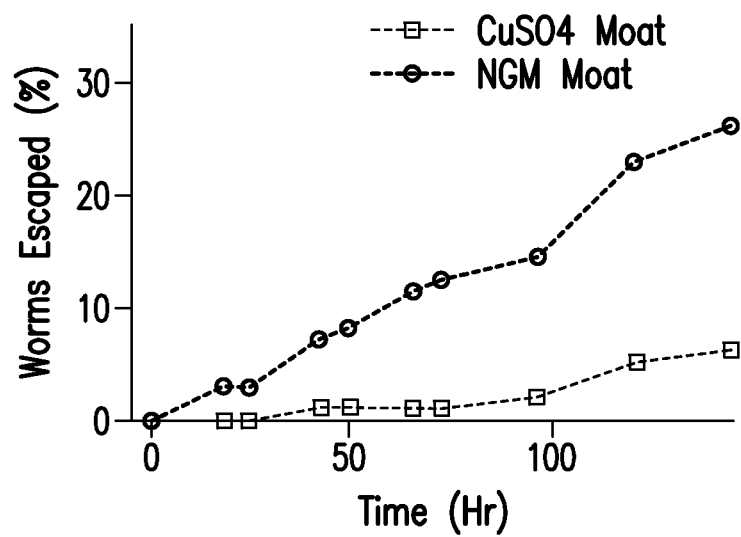
FIG. 7b shows the fraction of worms escaping wells as a function of time. A moat containing 100 mM $CuSO_4$ (red squares, n=96) is superior to a moat containing NGM buffer (blue circles, N=96) for preventing animals from leaving their wells. NGM buffer is NGM agar without agar, peptone, or cholesterol.

The WorMotel uses well geometry for improved worm cultivation and imaging of one worm per well. A rounded concave well geometry can reduce interference at the edge of the agar surface, and can inhibit worms from burrowing under the agar. Less than 5% of young adult worms in the WorMotel burrow beneath the agar after 24 hours in comparison with over 80% of worms in a conventional 384-well microplate (FIG. 7). To prevent worms from leaving their designated wells, moats consisting of NGM liquid were tested, but after 3 days about 20% of worms escaped into the liquid. By contrast, only 5% worms escaped after 3 days when moat containing 100 mM copper sulfate was used (FIG. 7). Thus, the WorMotel can longitudinally monitor up to 240 worms under near standard laboratory conditions with an attrition rate of about 5% over the course of early adulthood.

Figure 2A:
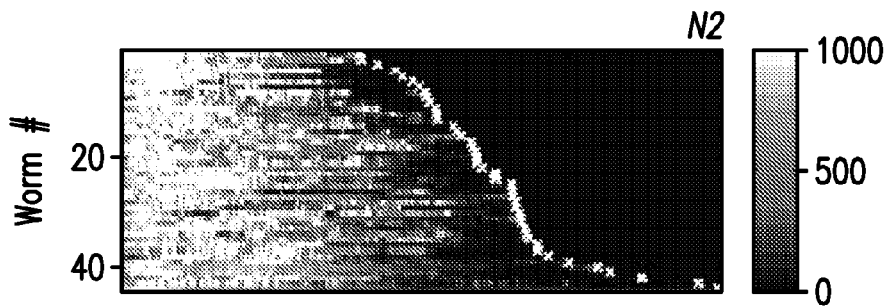
FIGS. 2a-b illustrate activity profiles for N2 and Hawaiian (CB4856) strains at 25° C. White indicates high activity and black indicates zero activity. Each row denotes the activity profile of a single worm. Worms are sorted by time of death. Time of death for each individual is marked by a white 'x'.
Figure 2B:
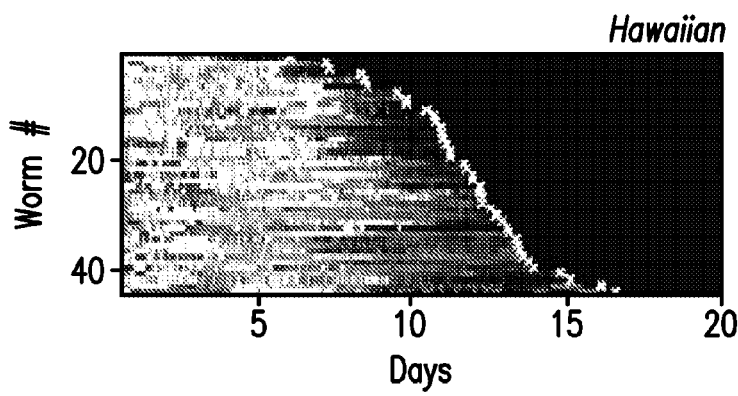
Figure 2C:
FIG. 2c shows an activity trace of a single N2 worm. Time of death is marked as the final moment of non-zero activity (arrow).
Figure 2D:
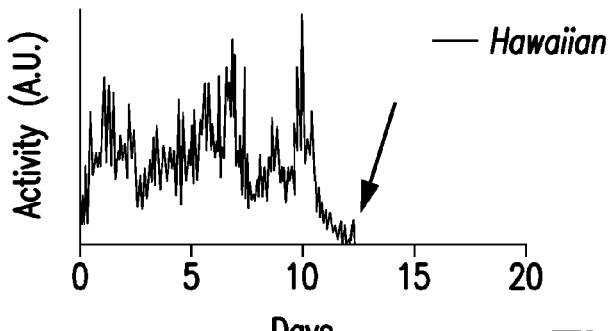
FIG. 2d shows an individual Hawaiian worm activity trace. Time of death is marked as the final moment of non-zero activity (arrow).
Figure 2E:
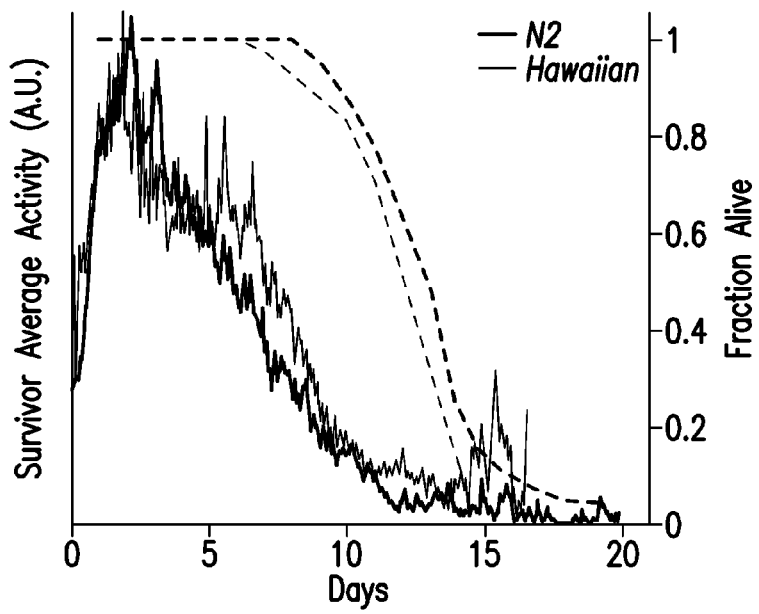
FIG. 2e shows average survivor activity (solid curves) and surviving fraction (dashed curves) plotted over time for N2 and Hawaiian.
Figure 8:
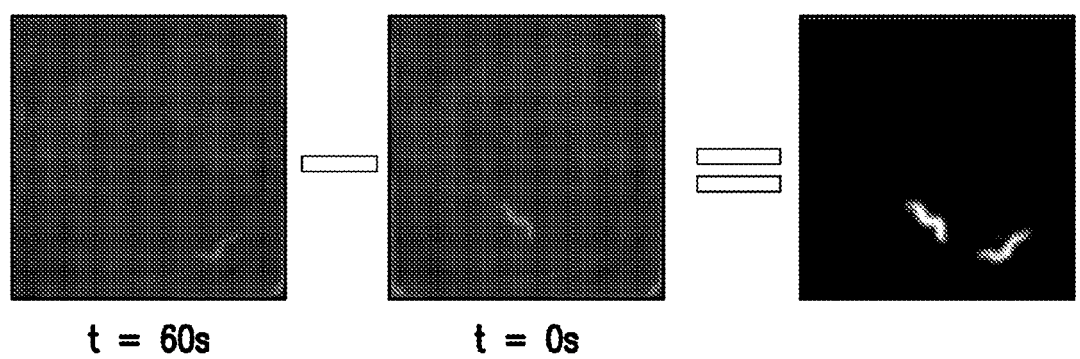
FIG. 8 illustrates activity quantification. Consecutive images (left and center) are subtracted to yield a map of pixel gray-scale intensity changes. The absolute value of these subtracted grayscale values are shown in the difference image (right). The number of pixels whose intensity changed above a threshold was summed up and the resultant value reported as 'activity'.
Figure 9A:
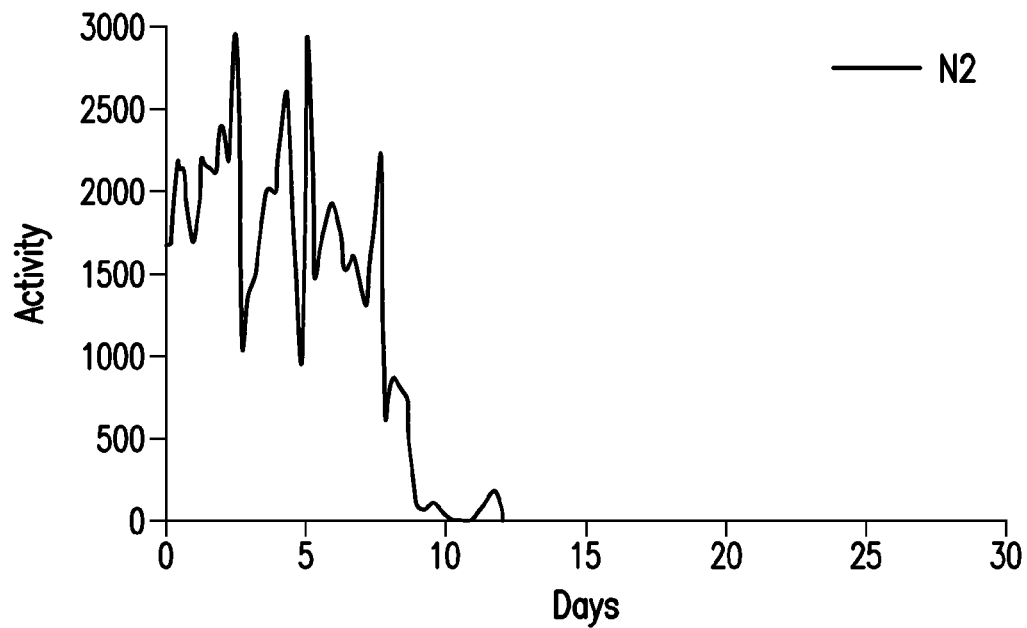
FIG. 9a shows activity measurements throughout life of an individual N2 worm at 25° C.
Figure 9B:
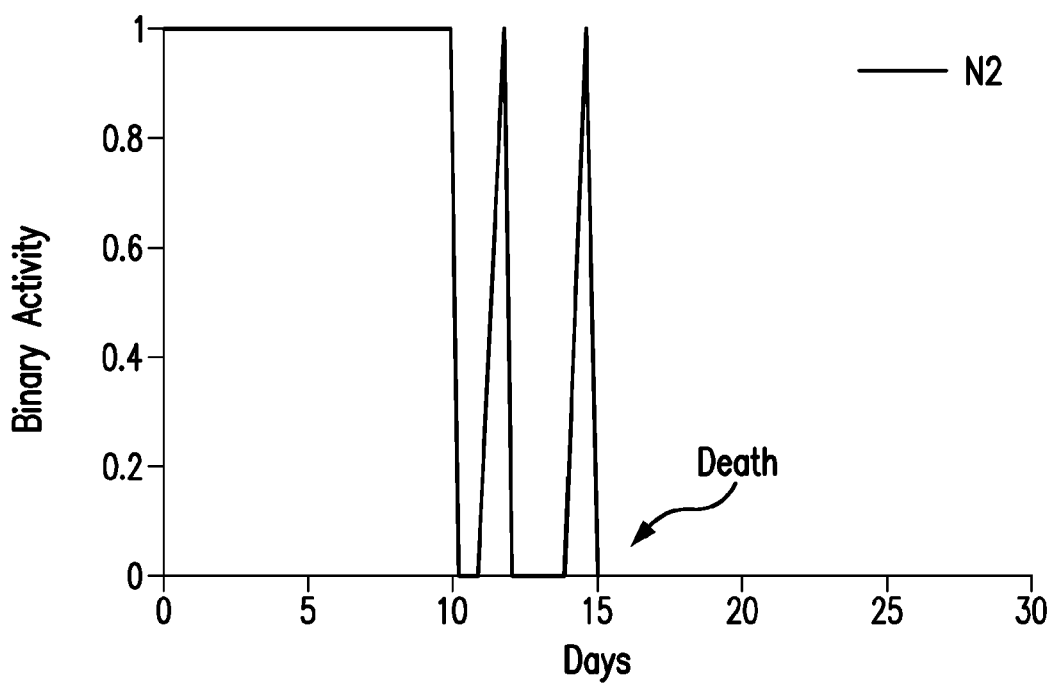
FIG. 9b illustrates that time of death was identified as the final moment the activity was greater than zero.

(1) The WorMotel Can Generate Life-Long Behavior Profiles And Enable Automated Lifespan Analysis To evaluate if the WorMotel could support worms throughout their lifespans, two strains were monitored: the reference strains N2 ("Bristol") and CB4856 ("Hawaiian"). Image data from the WM aging experiments was used to continuously track behavioral history of each animal throughout its adult lifespan. Activity level, defined as the number of pixels that had changed by more than a certain threshold between temporally-adjacent images was plotted (FIG. 2a-b, FIG. 8). The time of death was determined as the final time at which activity greater than zero occurred between images acquired one minute apart (FIG. 2c-d, FIG. 9). Activity profiles were averaged across individuals to generate behavioral healthspan curves and compare them to survival data (FIG. 2e).

Figure 2F:
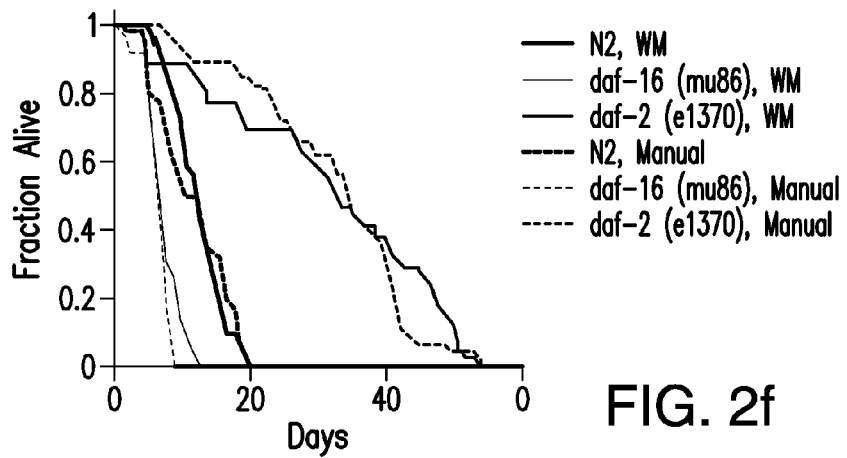
FIG. 2f shows survival curves for worms cultivated under standard laboratory conditions (dashed lines) and those grown on an example embodiment of the disclosed subject matter (solid lines). Worms were scored as dead by hand for manual assays and were automatically scored as dead by machine vision for the example embodiment of the disclosed subject matter.

To determine whether the WorMotel accurately reproduced the lifespans of worms grown under standard laboratory conditions used in most aging experiments, the survival curves of worms on standard agar plates to those grown in WorMotels were compared. The lifespans of N2 were measured alongside the short-lived strain daf-16 (mu86) and the long-lived strain daf-2 (e1370). For worms grown on standard plates, lifespan assays were carried out using standard methods. Mean lifespan of daf-16 animals (WM: 7.74±0.29 days, n=61; Manual: 6.98±0.15 days, n=117) was shorter than that of N2 (WM: 12.3±0.33 days, n=123; Manual: 12.15±0.51 days, n=94) while daf-2 showed a longer lifespan (WM: 33.5±1.94 days, n=46, Manual: 30.77±1.95 days, n=52) than N2. No significant difference between survival curves acquired from worms grown on standard plates and those grown on the WorMotel were found (FIG. 2f). These results show the WorMotel can reproduce expected lifespans for wild type as well as both short and long-lived strains and can monitor individual animals for at least 60 days.

Figure 2G:
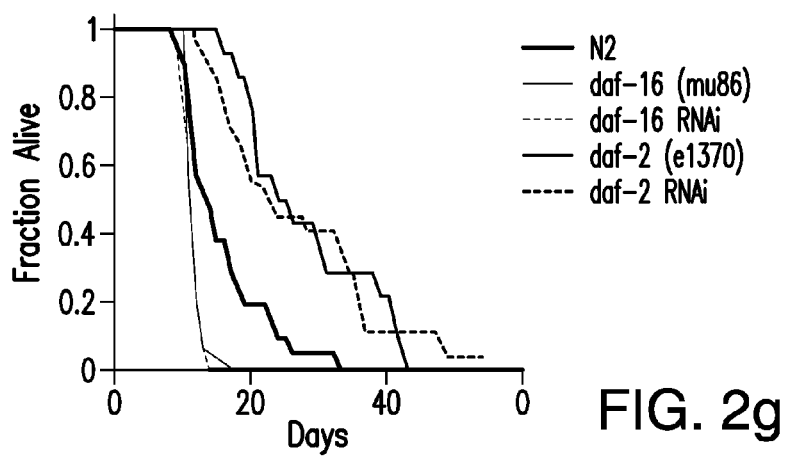
FIG. 2g shows survival data for worms cultivated with RNAi on an example embodiment of the disclosed subject matter. N2 and mutants (solid curves) were treated with an empty vector. N2 worms were fed either daf-2 or daf-16 RNAi (dotted curves). Temperature=20° C.

Next the compatibility of the WorMotel with methods for RNA interference was tested. Using RNAi by feeding, the lifespan of N2 in which either DAF-16 or DAF-2 was knocked down was measured. As a control, lifespans of N2, daf-16 (mu86), and daf-2 (e1370) fed with *E. coli* carrying an RNAi plasmid without a gene insert ("empty vector") were also measured. daf-16 (RNAi) and daf-16 (mu86) animals had a lifespan shorter than the empty vector control, and daf-2 (RNAi) and daf-2 (e1370)) animals lived longer than controls (FIG. 2g). These results show that the WorMotel platform is suitable for RNAi-based screening.

(2) Locomotion Profiles Can Predict Individual Worm Survival

Figure 3A:
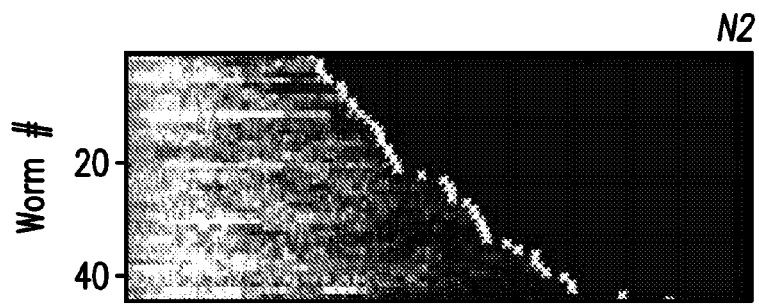
FIGS. 3a-d show activity profiles for N2 and three short-lived strains at 20° C. Time of death for each individual is marked by a white 'x'.
Figure 3B:
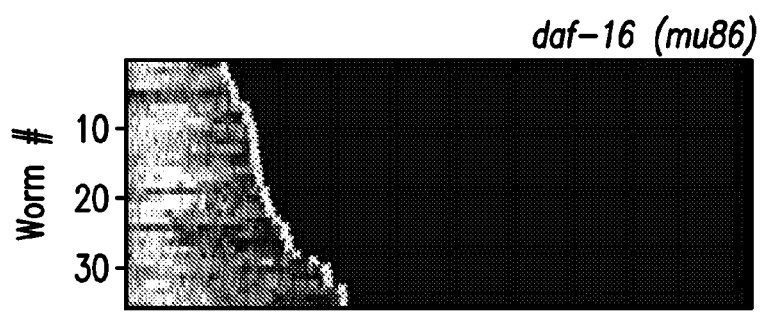
Figure 3C:
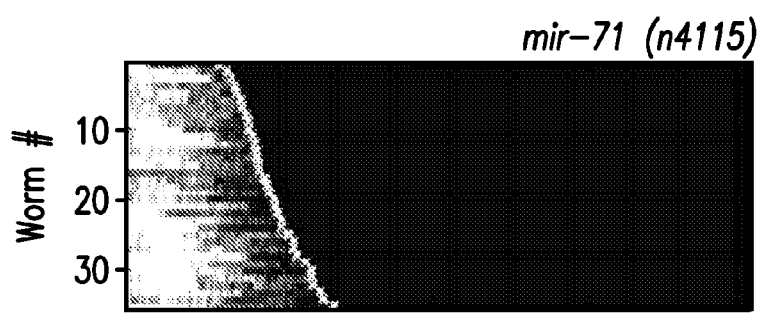
Figure 3D:
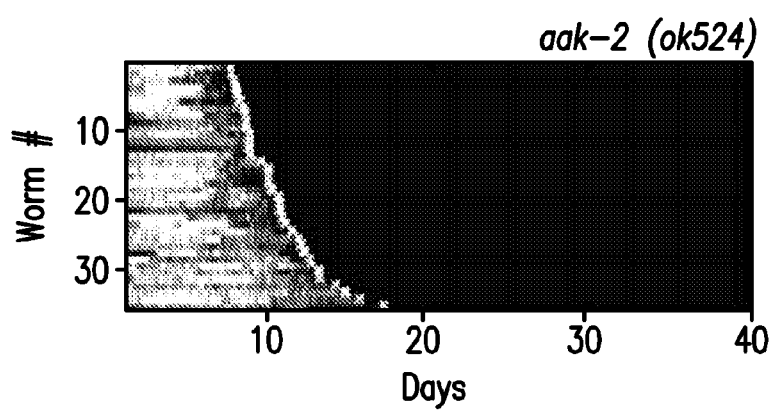
Figure 3E:
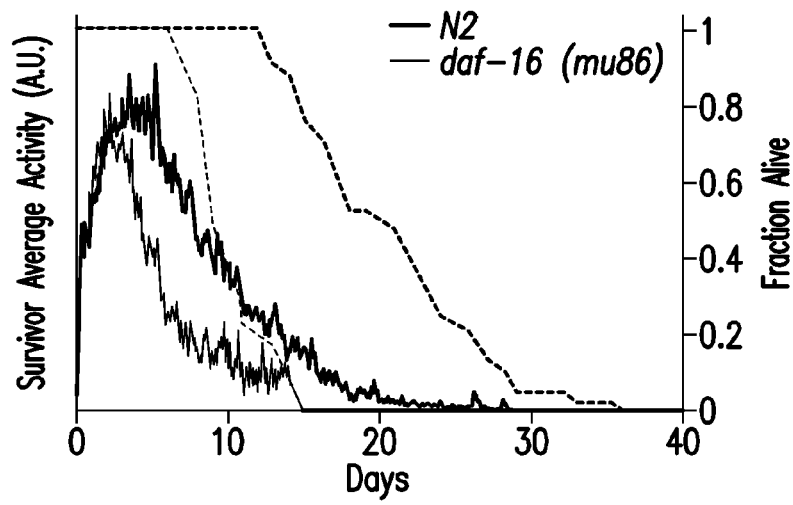
FIG. 3e shows survivor average activity (solid curves) and surviving fraction (dashed curves) for N2 and daf-16 (mu86). Average daf-16 activity is higher than N2 just before their respective deaths.
Figure 3F:
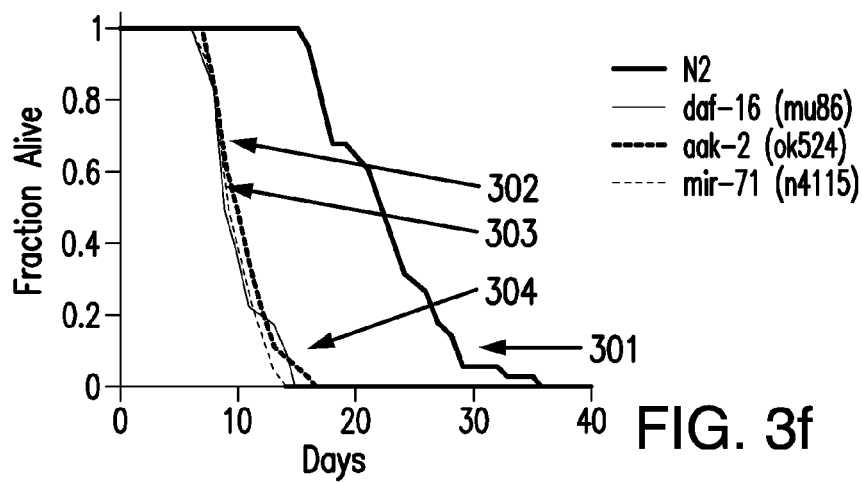
FIG. 3f shows survival curves for N2 and short-lived strains.
Figure 3G:
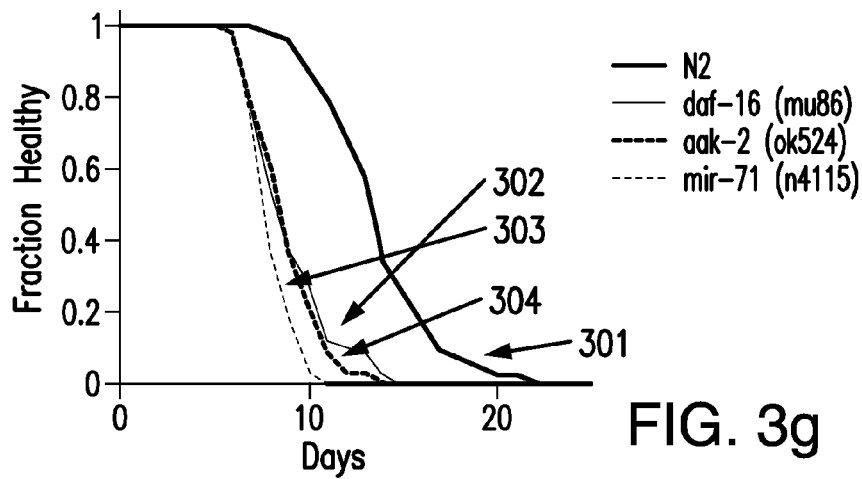
FIG. 3g shows healthspan curves for N2 short-lived strains.
Figure 3H:
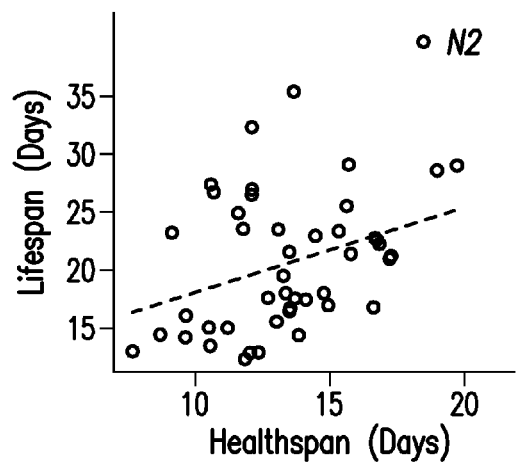
FIGS. 3h-k show lifespan versus healthspan for individual worms fitted to a line (dashed black line).
Figure 3I:
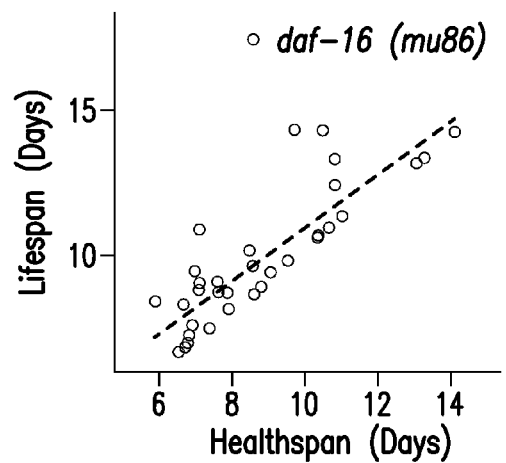
Figure 3J:
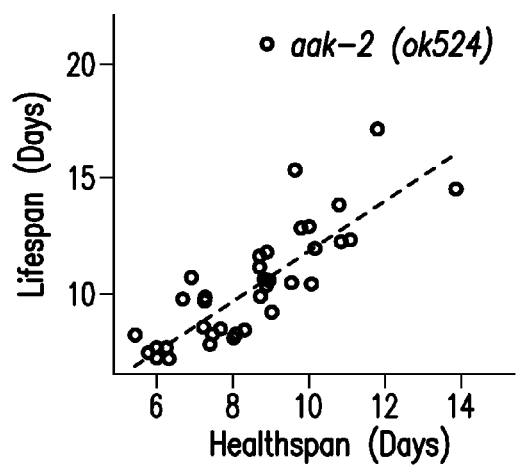
Figure 3K:
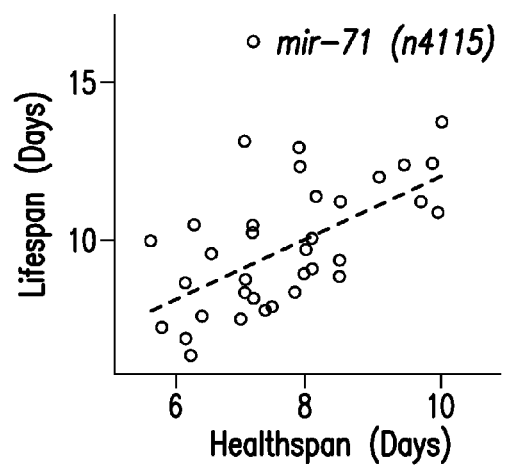
Figure 3L:
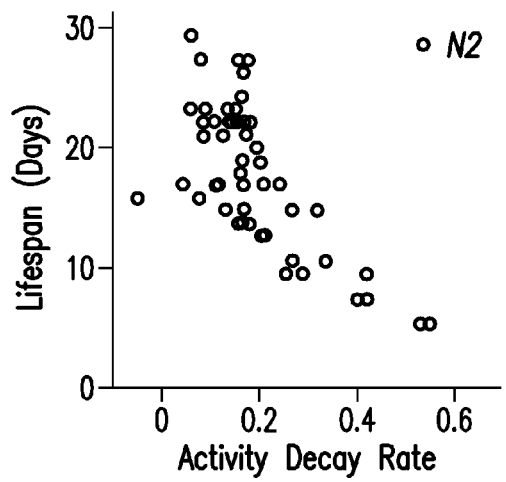
FIGS. 3l-o shows lifespan versus early life activity decay rate. Activity decay rate is the negative slope of individual activity traces during days 5-13 for N2 and days 2-6 for short-lived strains
Figure 3M:
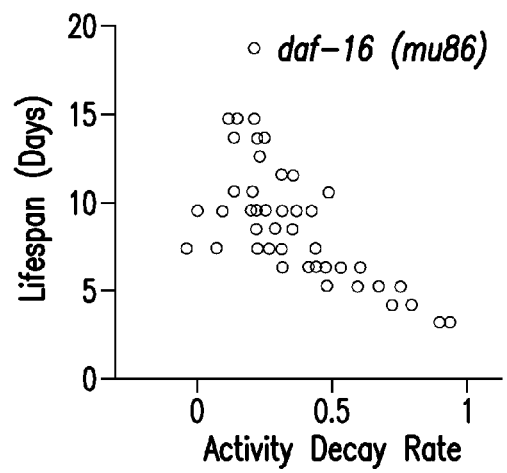
Figure 3N:
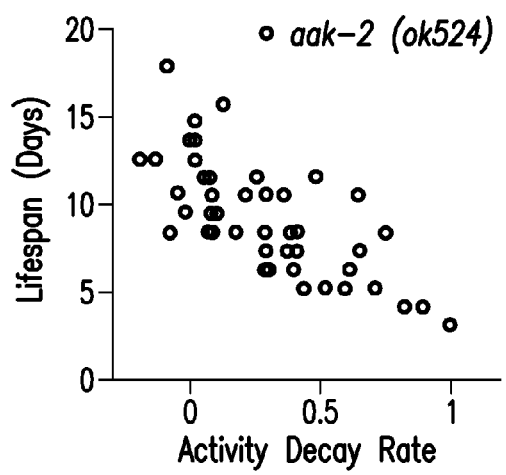
Figure 3O:
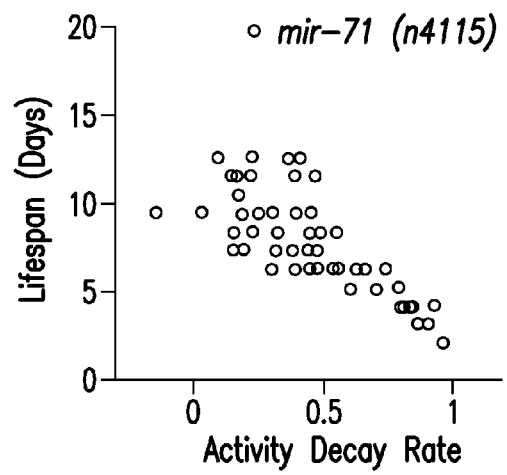

In order to characterize the utility of the locomotor activity profiles produced by the WorMotel, the three short-lived mutants daf-16 (mu86), mir-71 (n4115), and aak-2 (ok524) alongside N2 were monitored. Animals of these three mutant genotypes exhibited declines in their locomotion and died earlier than N2 animals (FIG. 3a-d, f, g) (N2 301; daf-16 302; mir-71 303; aak-2 304). The average survivor activity over time was plotted, however, short-lived mutants seemed to be healthier for a greater fraction of their lives compared to N2 (FIG. 3e). Each individual's healthspan was defined as the last time point at which its locomotion was greater than 50% of its maximum value. The fraction alive was plotted alongside the fraction healthy over time (FIG. 3f-g). Healthspan was well-correlated with lifespan for individuals within each strain (FIG. 3e-g). In all four strains, the curve depicting the fraction of healthy worms was shifted to the left of the curve depicting the fraction of live worms. As suggested by FIGS. 3e-g, the magnitude of this shift was greater for N2 than for the three short-lived mutants. These data suggest that while N2 animals live longer than these short-lived mutants, its fraction of life spent in good health might not be similarly prolonged.

The ability to track single animal trajectories throughout the adult life of the animal allowed an analysis of plotting individual lifespans as a function of their individual healthspan. The slope of a linear fit of these data was smaller for N2 animals (m=0.74) than for short-lived mutants (daf-16: m=0.92; aak-2: m=1.09; mir-71: m=0.96), suggesting that lifespan depends less strongly on healthspan in N2. Finally, the degree to which healthspan predicted lifespan, as reflected by the $R^2$ values of the least-squared linear regression fit, were larger for short-lived mutants (daf-16 $R^2$=0.71; aak-2 $R^2$=0.69; mir-71 $R^2$=0.34) than for N2 ($R^2$=0.12). Choosing a more lenient threshold for healthy activity, for example, 25% of maximum activity rather than 50%, was more predictive of lifespan for all these strains (N2 $R^2$=0.55; daf-16 $R^2$=0.86; aak-2 $R^2$=0.87; mir-71 $R^2$=0.61). This data shows that behavioral data from the WorMotel reflects the health of individual animals at specific time points during aging.

The rate of decay in locomotion during days 3 through 7 can be negatively correlated with lifespan. However, it was unclear whether the locomotion profiles produced by the WM could be used in this way to predict individual life spans. Activity decay rate was calculated as the negative slope of a line fit to the activity of individual worms early in life, defined as the time until 25% of each strain's animals had died, which was day 6 for the short-lived strains and day 13 for N2. We then plotted lifespan against the activity decay rate (FIG. 3l-o). Lifespan was indeed negatively correlated with early life activity decay rate (N2: R=0.70, p<$10^{-8}$; daf-16: R=0.61, p<$10^{-5}$; aak-2: R=0.42, p<0.005; mir-71: R=0.69, p<$10^{-8}$). These results indicate that activity measurements from the WM reflect the health trajectories of individual animals and can be used to identify healthy animals early in life.

Figure 4A:
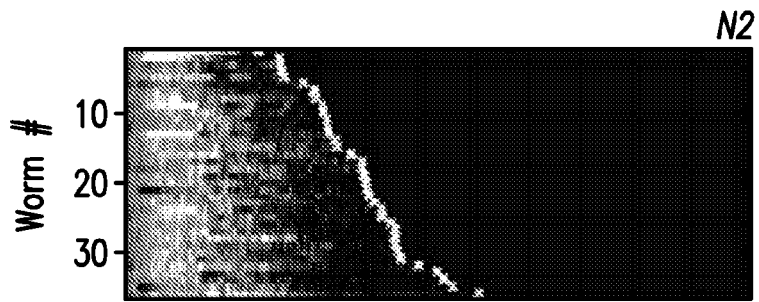
FIGS. 4a-d show activity profiles for N2 and three long-lived strains. White x's mark death.
Figure 4B:
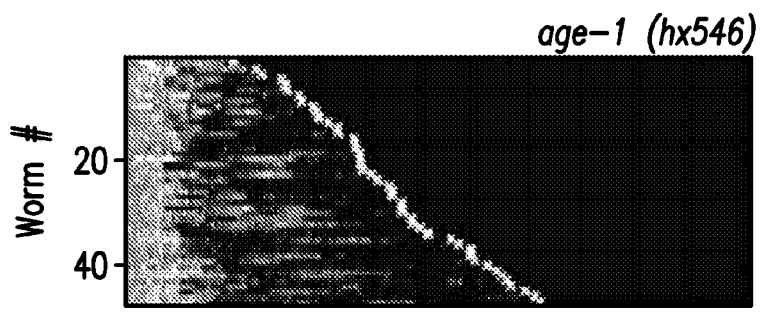
Figure 4C:
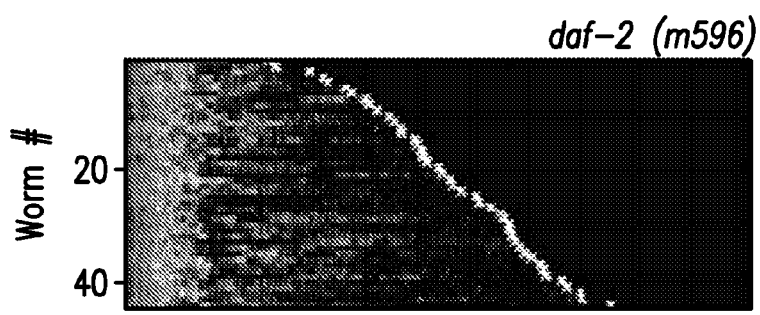
Figure 4D:
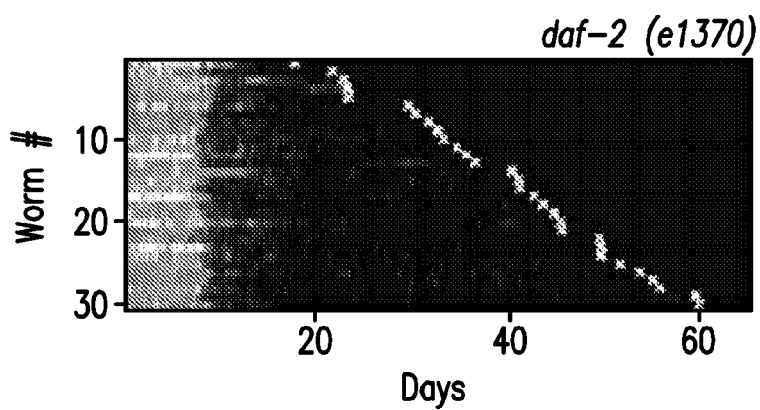
Figure 4E:
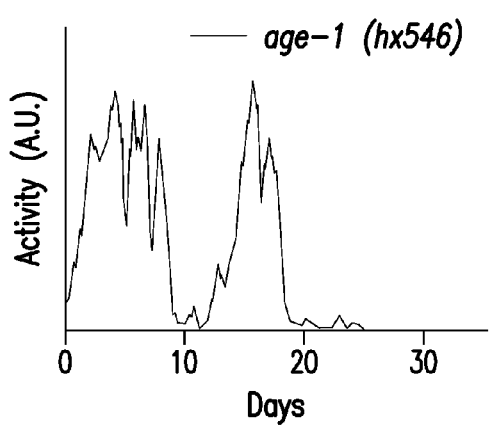
FIG. 4e shows an example age-1 mutant activity curve. Quiescence and revival are evident.
Figure 4F:
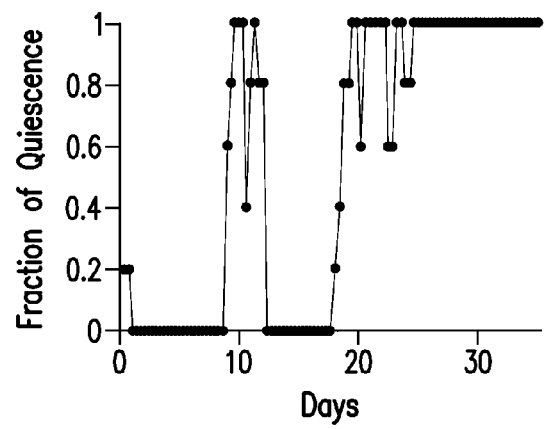
FIG. 4f shows the fraction of quiescence for the same worm as FIG. 4e. The fraction of quiescence increases greatly and then declines before the worm dies.
Figure 4G:
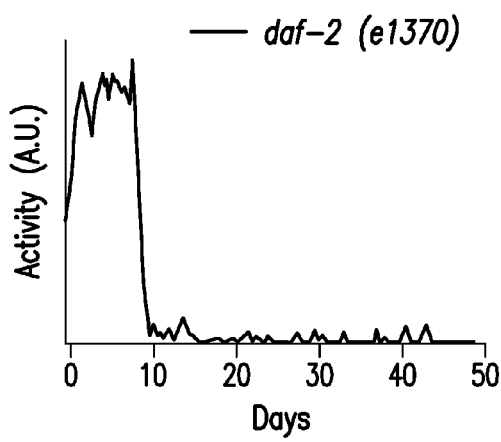
FIG. 4g shows an example daf-2 (e1370) activity curve. The precipitous decline in activity is evident on about day 10.
Figure 4H:
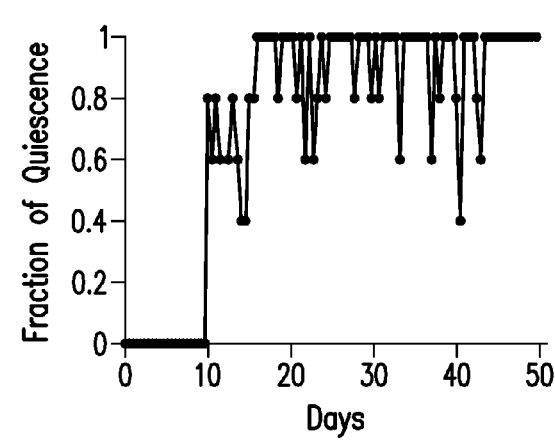
FIG. 4h shows the fraction of quiescence for the same worm as in FIG. 4g. The fraction of quiescence increases from 0 to about 1 on about day 10 and stays high until the worm dies on day 50.

(3) Monitoring of Individual Behavioral Profiles Can Reveal Unexpected Aging Phenotypes Some long-lived mutant strains exhibited striking differences in their behavioral aging profiles (FIG. 4a-d). Behavior of a mutant in the gene age-1, whose gene product encodes the *C. elegans* homolog of mammalian phosphatidylinositol-3-OH kinase (PI(3)K) catalytic subunit, was examined. Like other mutants in the insulin/insulin-like (IIS) signaling pathway, age-1 (hx546) animals have extended lifespan. age-1 worms show a decline in activity on around day 8 (day of initial decline=8.5±0.3 days) followed by a quiescent period of about 3 days (quiescent duration=2.8±0.5 days, FIG. 4e-f, l) during which worms exhibit essentially no movement. This quiescent period is followed by a revival during which animals resume activity approximately half the amplitude of the worm's peak activity from early adulthood (peak revival activity=44±4% of peak early life activity, FIG. 4e). Revivals occur in 72% (34/47) worms tested. This non-monotonic behavioral profile in age-1 worms supports the notion that long-term behavioral imaging can uncover novel phenotypes associated with aging.

Figure 4I:
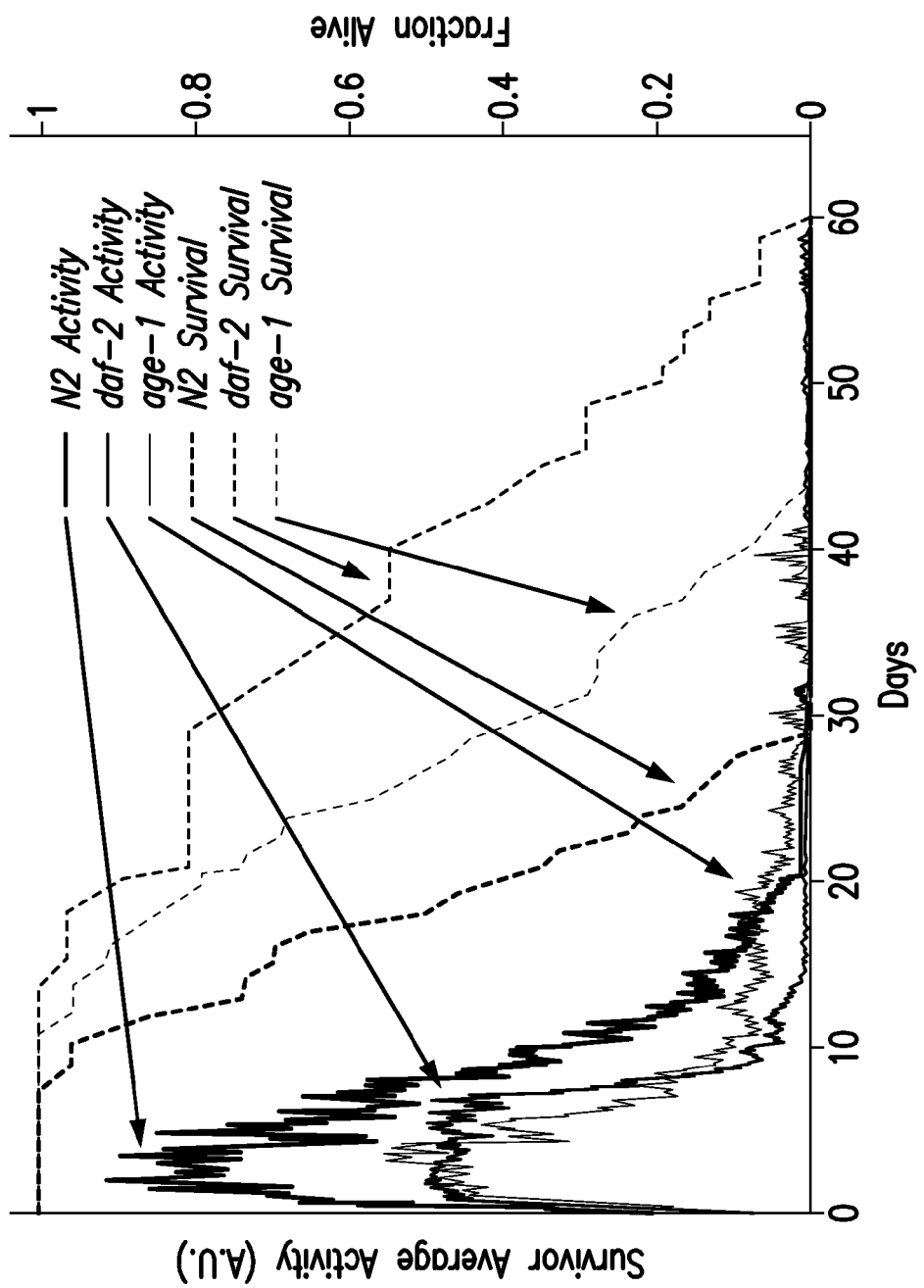
FIG. 4i shows survivor average activity (solid curves) and survival (dashed curves) for N2, age-1 (hx546), and daf-2 (e1370). age-1 revival is visible as a 'tail' to the right of the initial decline. daf-2 (e1370) decline together and do not revive.
Figure 4J:
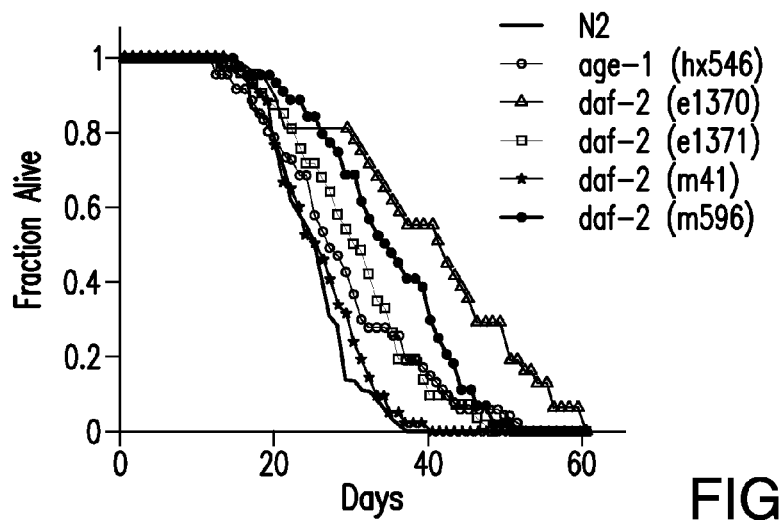
FIG. 4j shows survival curves for long-lived mutants.

Whether this mid-life quiescence in age-1 was common to all loss-of-function mutants in the IIS pathway was tested. The behavioral profile of mutants for the insulin receptor homolog daf-2, in which adult quiescence has previously been reported, was tested. daf-2 (e1370) worms exhibit a precipitous drop in activity around day 10 (FIG. 4d, g, h, l) and after that remain largely quiescent except for brief low-level bursts of activity until they die. By plotting survivor average activity along with survival it can be observed that the behavioral profiles of age-1 and daf-2 are different: the asynchronous revivals of age-1 animals lead to an extended period of activity during days 10-20, which was absent in daf-2 animals (FIG. 4i). Therefore, while age-1 and daf-2 worms both display more quiescence than N2, the collapse-and-revival behavior of age-1 mutants appears to be distinct from the pattern of quiescence in daf-2 animals.

Figure 4K:
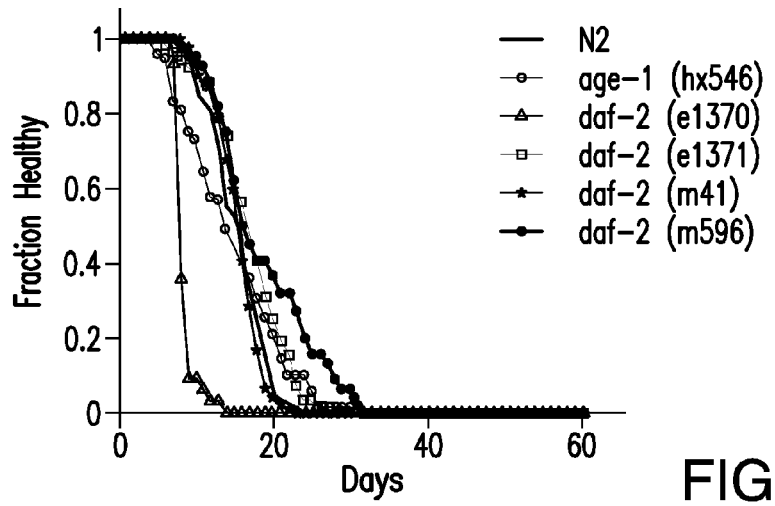
FIG. 4k shows locomotor healthspan curves for long-lived mutants.
Figure 4L:
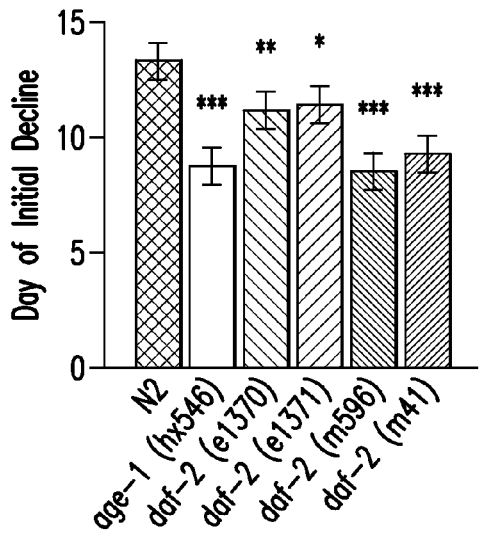
FIG. 4l shows the day of initial decline for long-lived mutants. *, $p<0.05$; , $p<0.01$; *, $p<0.001$. Error bars are s.e.m.
Figure 4M:
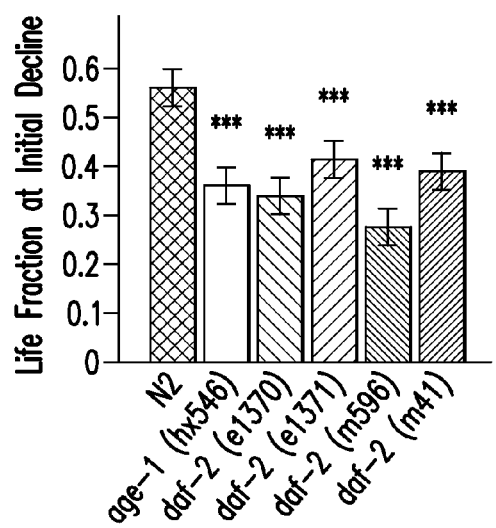
FIG. 4m shows the day of initial decline normalized by lifespan for each individual. ***, $p<0.001$. Error bars are s.e.m.
Figure 10:
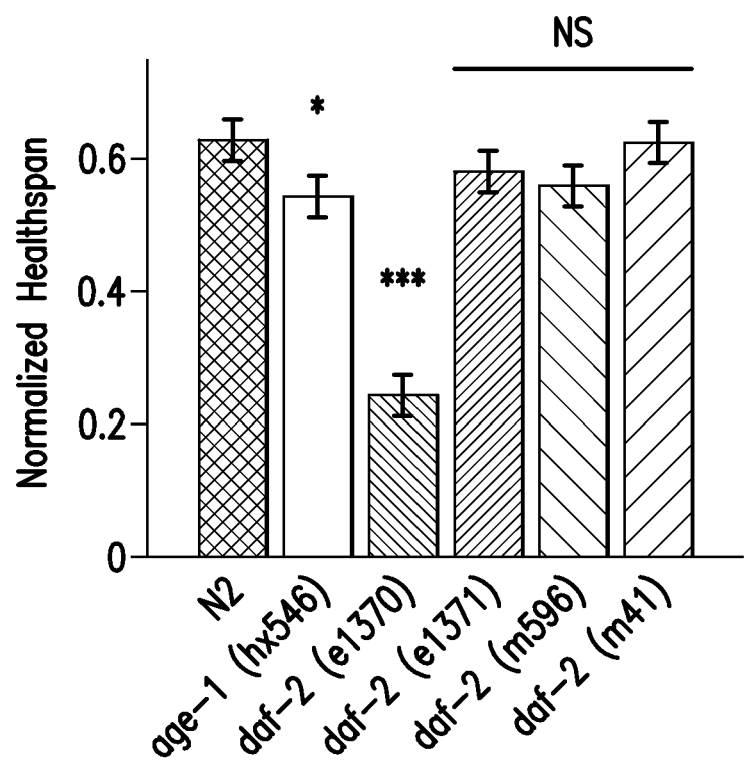
FIG. 10 illustrates the normalized healthspan of long-lived strains. Individual healthspan was divided by lifespan and strain averages are shown. Error bars are s.e.m. *$p<0.05$; ***$p<0.001$

In order to determine the relationship between healthspan and lifespan, survival for N2, age-1, and multiple alleles of daf-2, was plotted alongside the healthy fraction as determined by animals moving at greater than 50% of their maximum activity level. After normalizing individual healthspan by lifespan, only age-1 (hx546) and daf-2 (e1370) exhibit significant differences from N2 (FIG. 10). In order to further characterize the quiescence in these strains, the day of initial decline, the first time period of detectable prolonged quiescence, was quantified. All tested insulin-signaling mutants initially decline well before N2 (FIG. 4*l*) while most retain the ability to move normally (FIG. 4*k*). When the day of initial decline was normalized by the lifespan of individual animals, N2 first becomes quiescent on average at an age about 60% of its lifespan while age-1 and daf-2 mutants first become quiescent at an age between 30% and 40% of their lifespans (FIG. 4*m*). It is possible that prolonged quiescence can play a causal role in the long lifespan of insulin-signaling mutants. The WorMotel can play an important role in illuminating the role of such long-term phenotypes in extended longevity.

Figure 11A:
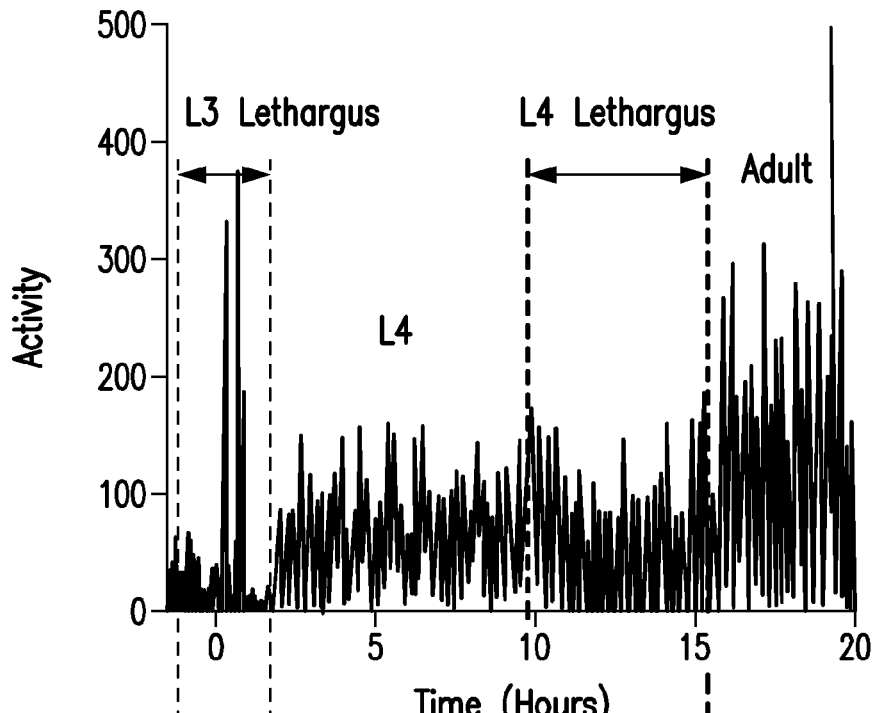
FIG. 11a shows an activity trace for a single worm from L3 until adulthood.
Figure 11B:
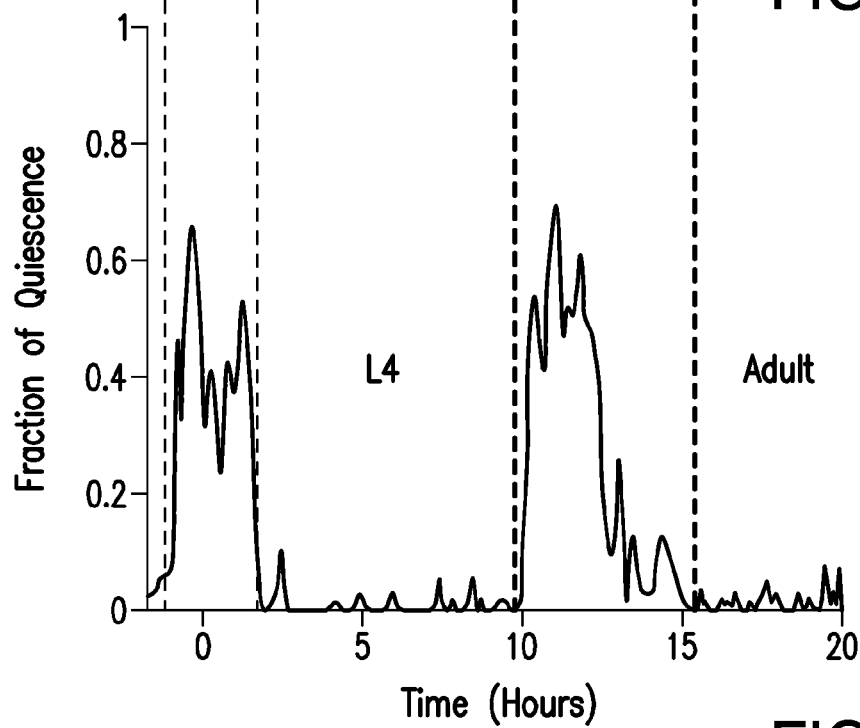
FIG. 11b shows the fraction of frames the worm in FIG. 11a was quiescent in a ten-minute moving window.
Figure 11C:
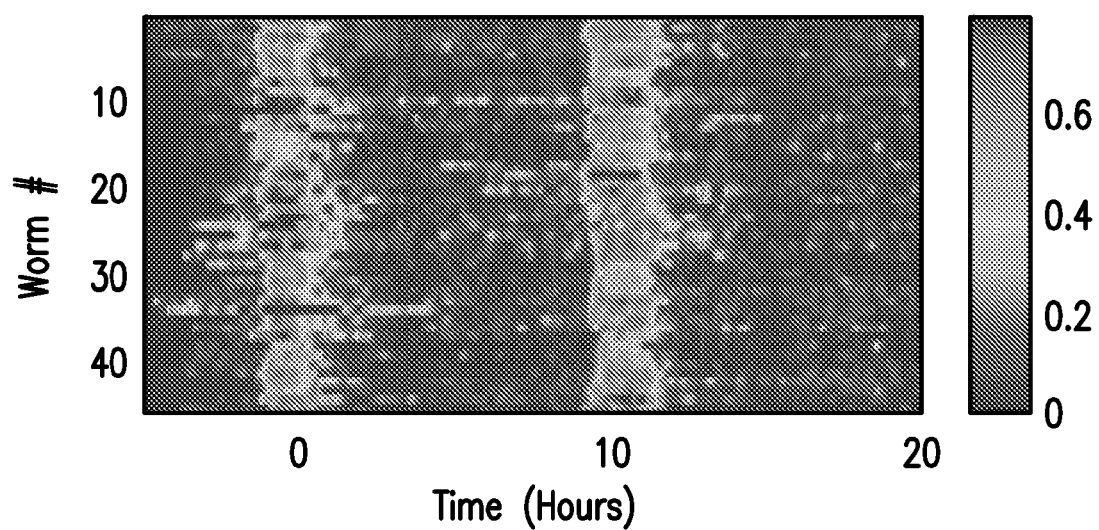
FIG. 11c shows the fraction of quiescence heat map for a single 48-well example embodiment of the disclosed subject matter initially filled with L3 worms. Warmer colors indicate more quiescence and cooler colors indicate less quiescence. The fraction of quiescence traces for each animal were aligned for visualization. The L3 lethargus and L4 lethargus are visible as two bands of high quiescence.
Figure 12:
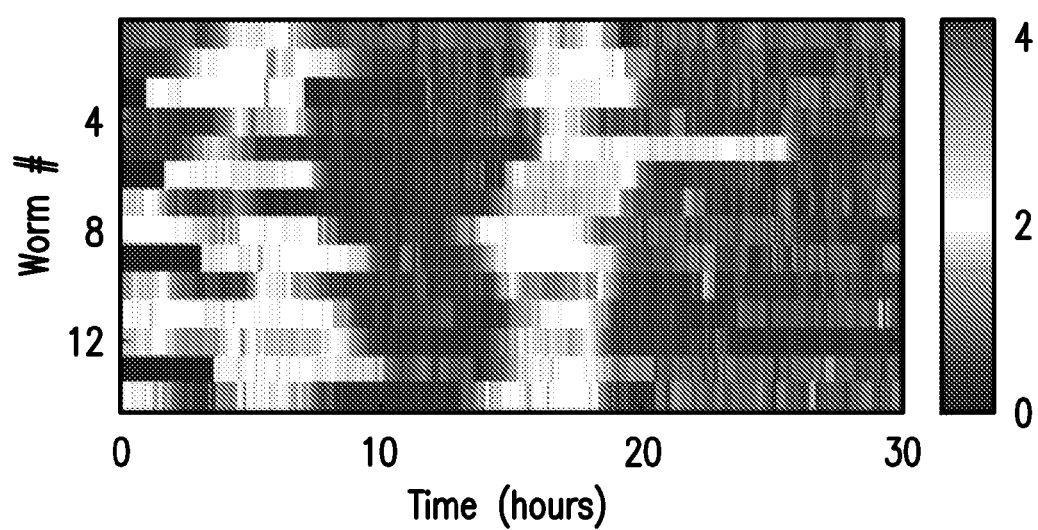
FIG. 12 shows long-term fluorescent reporter tracking with an example embodiment of the disclosed subject matter. mlt-10 is expressed in the hypodermis only during molting. Using a mlt-10::gfp reporter total worm fluorescence was tracked from the L3 stage to early adulthood. Heat map denotes fluorescence intensity in arbitrary units.
Figure 13:
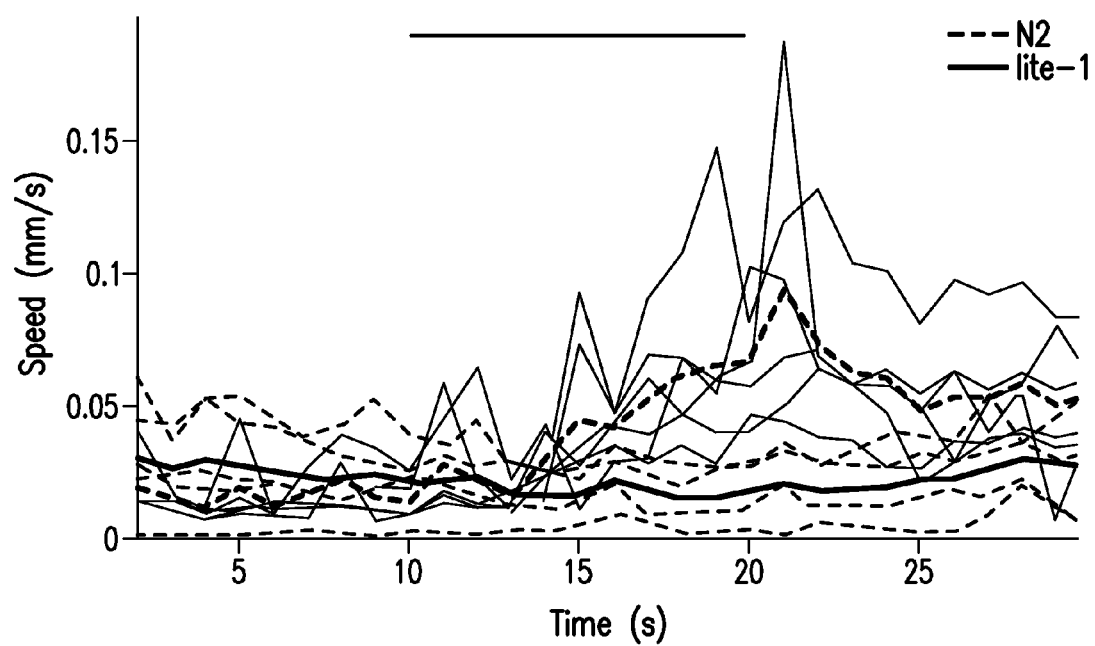
FIG. 13 illustrates measuring responses to aversive light stimulus. Violet light from an LED elicits an increase in speed in N2 worms. The light-sensing defective strain lite-1 exhibits an attenuated response to light. Young adult animals were imaged sequentially for 30 seconds under bright field illumination. Violet light stimulation lasted 10 seconds and began 10 seconds after imaging commenced. Speed traces for each animal represent an average of 40 trials. Strain averages are denoted in thick lines, and individual traces are denoted by thin black lines for N2 and dashed blue lines for lite-1. N=6 animals for each strain.
Figure 14A:
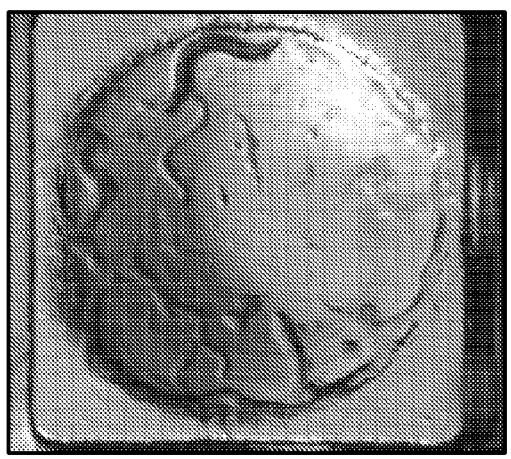
FIG. 14a shows a brightfield image of a single well with adult worm and FIG. 14b shows a darkfield image of the same well.
Figure 14B:
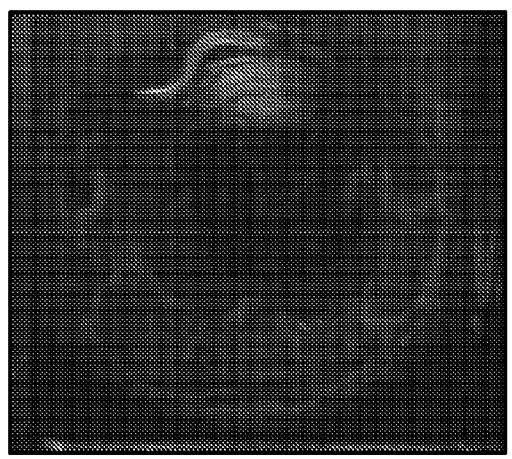

In addition to the applications to aging described here, the WorMotel method can be suited for other experiments in which longitudinal monitoring is desired. The disclosed subject matter has shown experiments in which the WorMotel was used to measurement of quiescence during development (FIG. 11), long-term monitoring of fluorescent reporters (FIG. 12) and monitoring responses to aversive stimuli (FIG. 13).

B. Construction & Use of WorMotel (1) WorMotel Design and Fabrication

Using MATLAB scripts, a chip containing a rectangular array of either 48 or 240 rounded wells with 3 mm diameter, 3 mm depth, and center-to-center spacing of 4.5 mm (FIG. 5*a*) was designed. Each well was surrounded by a 0.5 mm wide and 3 mm deep 'moat'. A master corresponding to the negative of this shape in the material VeroBlack was fabricated using an Objet30 photopolymer 3D printer (Stratasys). (FIG. 5*b*).

To mold the PDMS devices, Sylgard 184 PDMS (Dow Corning) was mixed according to the manufacturer's instructions, bubbles were removed by vacuum degassing for 15 min, and then an appropriate amount of PDMS was poured into the masters. Devices were cured overnight at 40 C then removed from molds using a spatula. The first device cast from each master often did not de-mold cleanly, but subsequent casts were successful (FIG. 5*c*).

(2) WorMotel Preparation

To prepare devices for experiments, the chips were first treated with oxygen or air plasma for 3 minutes using a plasma cleaner (PE-50, Plasma Etch Inc.). This treatment can render PDMS temporarily hydrophilic, which can improve the ease of filling of wells and moats. The medium was based on standard NGM media except low-gelling temperature agarose (Gelling temp. 26-30° C., Research Products International) was substituted for agar to facilitate filling by pipette and streptomycin (200 ng/mL) was added to the medium to minimize bacterial contamination.

For aging experiments 5-fluoro-2'-deoxyuridine (FUdR) was added to prevent progeny growth. An FUdR stock solution of 10 mg/ml was prepared and added to molten agar at a concentration of 2.5 μL per mL just prior to filling. This yielded a final concentration of FUdR of 100 μM.

After the agar cooled and gelled, a suspension of the *Escherichiae coli* bacterial strain DA837, which is a streptomycin resistant derivative of OP50 (Brenner, S. The Genetics of *C. elegans. Genetics* 77, 71-94 (1974)) was added to each well using a 200 μL pipette.

A moat solution of 100 mM $CuSO_4$ was prepared, which was approximately in osmotic equilibrium with the agar medium. The moat solution was added to the moats by pipette.

For aging experiments, late L4 worms were added to the WorMotel either manually with a platinum wire pick or automatically using a COPAS Biosort machine (Union Biometrica).

Figure 5D:
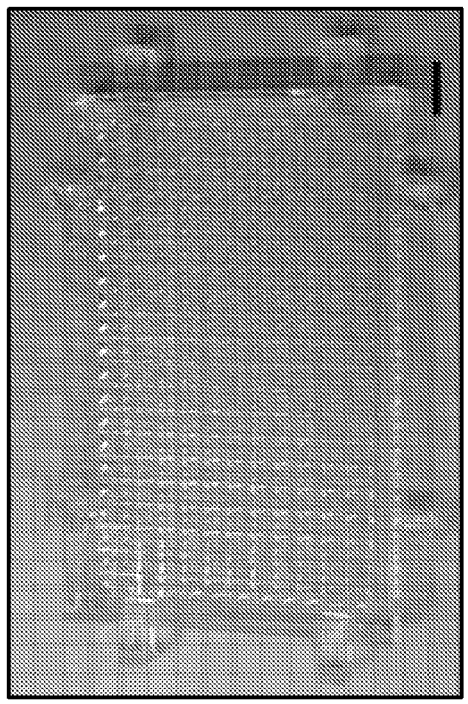
FIG. 5d shows an example embodiment of the disclosed subject matter mounted in an OmniTray
Figure 6A:
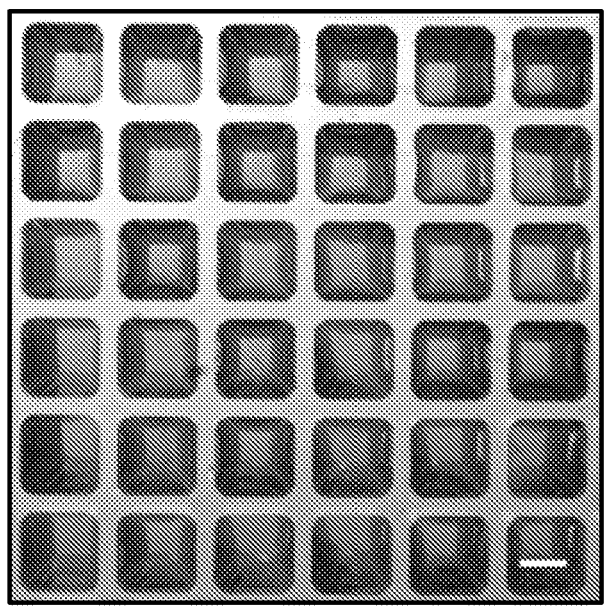
FIG. 6a shows a bright field image of L4 worms crawling on agar in a polystyrene 384-well plate (Corning Costar). Worms are obscured by edges of wells. Darkfield images resulted in extremely poor image quality (not shown). Scale bar: 2 mm.
Figure 6B:
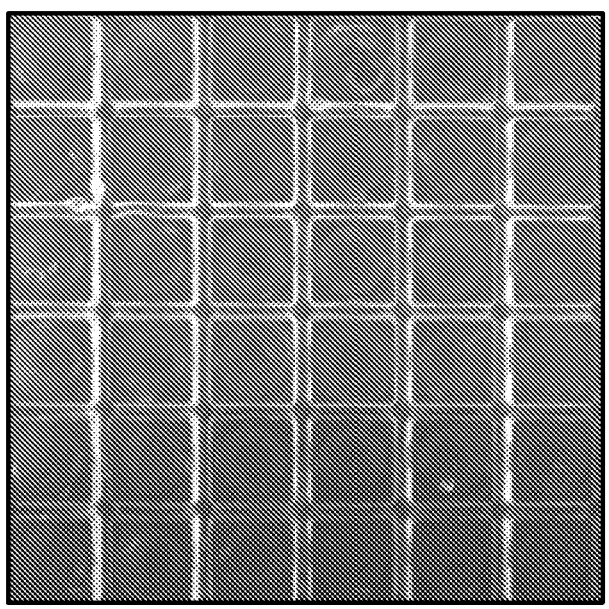
FIG. 6b shows a darkfield image of L4 worms on agar in an example embodiment of the disclosed subject matter. Well design enables more uniform illumination and easy identification of worms.

PDMS devices were placed inside either a 90 mm diameter Petri dish for 48-well WorMotels or an OmniTray microplate (Nunc Thermo Scientific) for 240-well. 240-well WorMotels contained alignment tabs to keep devices in alignment with respect to the OmniTray (FIG. 5*d*). To maintain humidity inside the dishes, water absorbing sodium polyacrylate crystals were used. Sterile distilled water was added to the crystals in a ratio of 30:1 (water:crystals) by weight. Approximately 15 g of hydrated crystals were added around the WorMotel. Lids were placed on all dishes. For aging experiments, a single layer of fully-stretched Parafilm (Bemis Co.) was wrapped around the sides of the plate to further reduce water loss while permitting gas exchange.

(3) Image Acquisition

Images were captured with an Imaging Source DMK 72AUC02 camera (2592×1944 pixels) equipped with a Fujinon lens (HF12.5SA-1, 1:1.4/12.5 mm). IC Capture software (The Imaging Source) was used to acquire time lapse images. All experiments were carried out under darkfield illumination using four 4.7" long red LED strips (Oznium) positioned approximately 2" below the WorMotel. Images were saved and processed by a 64-bit computer with a 3.40 GHz Intel Core i3 processor and 4 GB of RAM. Images were analyzed using custom MATLAB software.

Different spatial resolutions can be attained by adjusting the camera's field of view and thus by modulating the number of wells viewed at once. Imaging 6 wells at once gives approximately 5 μm resolution, imaging 12 wells gives 7 μm resolution, imaging 48 wells gives 15 μm resolution, and imaging 240 wells gives 36 μm resolution.

(4) Image Processing

Temporally adjacent images were subtracted to generate maps of pixel value intensity change (FIG. 8). A Gaussian smoothing filter with width 3-5 pixels was applied to the resulting image in order to reduce camera noise. A binary threshold was then applied to the filtered intensity change image in order to score whether or not movement occurred at each pixel: those pixels which changed by much more than the noise level of the camera. All pixels in which movement occurred were counted and the resulting value was called the 'activity' between the two frames.

(5) Removal of Camera Artifacts

Approximately 0.17% of frames, in which camera errors resulted in shifted or distorted images, were censored. These events were automatically identified based on activity spikes above threshold occurring simultaneously across all regions of interest.

(6) Automatic Death Quantification

Time of death was quantified as the final time point during which the activity was greater than zero (FIG. 9).

(7) Healthspan Calculation

Activity profiles were normalized to the maximum for each individual worm. The healthspan was defined as the final time point at which the individual's activity value was greater than or equal to 50% of its maximum value.

(8) Lifespan Prediction by Activity Decay Rate

Early life was defined as day 2 until the $25^{th}$ percentile of lifespan for each strain tested. This time point corresponded to day 13 for N2, day 6 for daf-16, day 6 for aak-2, and day 6 for mir-71. For each individual, the normalized activity during early life was fit by a linear function. The negative slope of the fit line was taken as the early life activity decay rate. Lifespan was then plotted against early life activity decay rate. A line was fit to the data and the $R^2$ value was generated for each strain (FIG. 3*l-o*).

(9) Fraction of Quiescence and Day of Initial Decline Calculation

The fraction of quiescence was calculated by tallying the fraction of frames in a two-hour window during which the activity was less than a specified threshold (FIG. 4). The day of initial decline was calculated for each individual by measuring the first time point at which the fraction of quiescence rose above 0.5.

(10) Automated Imaging of Multiple Plates

A plate handler robot (Caliper Twister II) was used to automatically image multiple plates per day by sequentially lifting each plate from a stack and positioning it inside a dark field imaging rig for 10 minutes (FIG. 1*c*). The Twister II has a capacity of 400 plates, and can monitor 96,000 individual worms. Multiple OmniTrays containing prepared WorMotels were placed in a 'home' stack. The robot lifted each plate and positioned it in a darkfield imaging rig for 10 minutes at which point the plate was returned to an 'away' stack. Once all plates in the 'home' stack had been imaged, the plates in the 'away' stack were returned to the 'home' stack and the loop began again. The camera acquired images continuously throughout this plate rotation process. Plates were uniquely identified in each image via a printed barcode located at the top of each plate.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

What is claimed is:

1. An apparatus, comprising:
a substrate having a planar array of conical-shaped depressions, wherein each depression is defined by an upper opening, a concave side wall and a bottom surface, wherein the substrate further comprises a network of channels that are arranged in a grid-like structure and are interconnected to form a continuous path through the substrate, wherein the channels are disposed around each depression of said array of depressions to form a dedicated moat for each depression; and
a tray, wherein said substrate is configured to be inserted into said tray.

2. The apparatus of claim 1, wherein the depressions have a 3 mm diameter, a 3 mm depth, and a center-to-center spacing of 4.5 mm.

3. The apparatus of claim 2, wherein the moats disposed around each depression are 0.5 mm wide and 3 mm deep.

4. The apparatus of claim 1, wherein the substrate is made of at least one of polyurethane, polycarbonate, polyvinyl, polystyrene, polyvinylchloride (PVC), polypropylene, polydimethylsiloxane (PDMS), and cyclic olefin copolymer (COC).

5. The apparatus of claim 1, wherein the substrate is of uniform thickness.

6. The apparatus of claim 5, wherein the substrate is made entirely of polyurethane, polycarbonate, polyvinyl, polystyrene, polyvinylchloride (PVC), polypropylene, or cyclic olefin copolymer (COC).

7. The apparatus of claim 6, wherein the substrate is made of polystyrene.

8. The apparatus of claim 1, wherein the substrate has an overall shape and dimension generally conforming to a standard ANSI/SLAS microplate.

9. The apparatus of claim 8, wherein the standard ANSI/SLAS microplate comprises at least one of a 48-well microplate having a 8×6 array of wells; a 96-well microplate having a 8×12 array of wells; a 240-well microplate having a 12×20 array of wells; and a 384-well microplate having a 16×24 array of wells.

10. The apparatus of claim 1, wherein the insertion of the substrate into the tray creates a space disposed about the substrate.

11. The apparatus of claim 10, further comprising a plurality of water-absorbing crystals disposed about the substrate.

* * * * *